(12) United States Patent  
Marcusson et al.

(10) Patent No.: US 8,846,631 B2  
(45) Date of Patent: Sep. 30, 2014

(54) MICRORNA COMPOSITIONS AND METHODS

(75) Inventors: Eric G. Marcusson, San Diego, CA (US); Balkrishen Bhat, San Diego, CA (US); Peter Linsley, San Diego, CA (US); Akin Akinc, Cambridge, MA (US)

(73) Assignee: Regulus Therapeutics Inc., San Diego, CA (US)

( * ) Notice: Subject to any disclaimer, the term of this patent is extended or adjusted under 35 U.S.C. 154(b) by 0 days.

(21) Appl. No.: 13/521,597

(22) PCT Filed: Jan. 14, 2011

(86) PCT No.: PCT/US2011/021287

§ 371 (c)(1),  
(2), (4) Date: Jan. 24, 2013

(87) PCT Pub. No.: WO2011/088309

PCT Pub. Date: Jul. 21, 2011

(65) Prior Publication Data

US 2013/0123329 A1    May 16, 2013

Related U.S. Application Data

(60) Provisional application No. 61/295,121, filed on Jan. 14, 2010, provisional application No. 61/317,126, filed on Mar. 24, 2010, provisional application No. 61/325,747, filed on Apr. 19, 2010.

(51) Int. Cl.

| | |
|---|---|
| *C12N 15/11* | (2006.01) |
| *A61K 48/00* | (2006.01) |
| *C07H 21/02* | (2006.01) |
| *C07H 21/04* | (2006.01) |

(52) U.S. Cl.  
USPC ......................... 514/44 A; 536/24.5

(58) Field of Classification Search  
USPC ............................ 514/44; 536/24.5  
See application file for complete search history.

(56) References Cited

U.S. PATENT DOCUMENTS

| | | |
|---|---|---|
| 7,074,622 B2 | 7/2006 | Qiao et al. |
| 7,365,058 B2 | 4/2008 | Stoffel et al. |
| 7,683,036 B2 | 3/2010 | Bennett et al. |
| 7,723,030 B2 | 5/2010 | Croce et al. |
| 7,772,389 B2 | 8/2010 | Tuschl et al. |
| 7,888,010 B2 | 2/2011 | Brown et al. |
| 7,960,359 B2 | 6/2011 | Brown et al. |

(Continued)

FOREIGN PATENT DOCUMENTS

| | | |
|---|---|---|
| WO | WO 2004/076622 | 9/2004 |
| WO | WO 2005/013901 | 2/2005 |

(Continued)

OTHER PUBLICATIONS

Andreakos et al., "Amphoteric Liposomes Enable Systemic Antigen-Presenting Cell—Directed Delivery of CD40 Antisense and Are Therapeutically Effective in Experimental Arthritis," Arthritis & Rheumatism, 2009, 60(4):994-1005.

(Continued)

*Primary Examiner* — Terra Cotta Gibbs  
(74) *Attorney, Agent, or Firm* — Casimir Jones, S.C.

(57) ABSTRACT

Provided herein are compositions comprising oligomeric compounds. In certain embodiments, the oligomeric compounds are useful as miRNA mimics. The oligomeric compounds may mimic the activity of miR-34. Also provided herein are methods for the treatment of cancer.

15 Claims, 3 Drawing Sheets

Circulating human aFP levels increased with time in animals with established orthotopic liver tumors.

(56) References Cited

U.S. PATENT DOCUMENTS

| | | | |
|---|---|---|---|
| 8,058,250 | B2 | 11/2011 | Brown et al. |
| 8,071,562 | B2 | 12/2011 | Bader et al. |
| 8,088,749 | B2 | 1/2012 | Simeone et al. |
| 8,106,180 | B2 | 1/2012 | Chen et al. |
| 8,137,910 | B2 | 3/2012 | Cullen et al. |
| 8,148,069 | B2 | 4/2012 | Croce et al. |
| 8,158,601 | B2 | 4/2012 | Chen et al. |
| 8,173,611 | B2 | 5/2012 | Brown et al. |
| 8,367,628 | B2 | 2/2013 | Goodwin et al. |
| 8,378,088 | B2 | 2/2013 | Cleary et al. |
| 8,389,486 | B2 | 3/2013 | Lieberman et al. |
| 8,399,248 | B2 | 3/2013 | Cleary et al. |
| 8,563,708 | B2 | 10/2013 | Brown et al. |
| 8,586,727 | B2 | 11/2013 | Kelnar et al. |
| 2004/0203145 | A1 | 10/2004 | Zamore et al. |
| 2005/0059024 | A1 | 3/2005 | Conrad |
| 2005/0182005 | A1 | 8/2005 | Tuschl et al. |
| 2009/0227533 | A1 | 9/2009 | Bader et al. |
| 2009/0306194 | A1 | 12/2009 | Ford et al. |
| 2010/0104662 | A1 | 4/2010 | Oren et al. |
| 2011/0313025 | A1 | 12/2011 | Brown et al. |
| 2012/0065248 | A1 | 3/2012 | Brown et al. |
| 2012/0276627 | A1 | 11/2012 | Kelnar et al. |
| 2012/0282696 | A1 | 11/2012 | Johnson et al. |

FOREIGN PATENT DOCUMENTS

| | | |
|---|---|---|
| WO | WO 2005/078139 | 8/2005 |
| WO | WO 2005/118806 | 12/2005 |
| WO | WO 2006/013022 | 2/2006 |
| WO | WO 2006/137941 | 12/2006 |
| WO | WO 2007/064857 | 6/2007 |
| WO | WO 2008/073922 | 6/2008 |
| WO | WO 2008/088858 | 7/2008 |
| WO | WO 2008/092099 | 7/2008 |
| WO | WO 2008/104974 | 9/2008 |
| WO | WO 2008/137862 | 11/2008 |
| WO | WO 2008/137867 | 11/2008 |
| WO | WO 2008/154333 | 12/2008 |
| WO | WO 2009/086558 | 7/2009 |
| WO | WO 2009/111658 | 9/2009 |
| WO | WO 2009/134487 | 11/2009 |
| WO | WO 2009/149418 | 12/2009 |
| WO | WO 2010/042877 | 4/2010 |
| WO | WO 2010/048536 | 4/2010 |
| WO | WO 2010/129687 | 11/2010 |
| WO | WO 2012/106591 | 8/2012 |
| WO | WO 03/029459 | 4/2013 |

OTHER PUBLICATIONS

Bader et al., "The Promise of MicroRNA Replacement Therapy," Cancer Res., 2010, 70:7027-7030.
Bader et al., "Developing therapeutic microRNAs for cancer," Gene Therapy, 2011, 18:1121-1126.
Bader et al., "The Therapeutic Potential of microRNAs," Innovations Pharm Tech., Mar. 2011, pp. 52-55.
Christoffersen et al., "p53-independent upregulation of miR-34a during oncogene-induced senescence represses MYC," Cell Death and Differentiation, 2010, 17:236-245.
Daige et al., "microRNA mimics as cancer therapeutics," Abstract #268, RNA Silencing: Mechanism, Biology and Application, Keystone Symposium, Jan. 14-19, 2010, 1 page.
Marcusson et al., "microRNA Mimics As Cancer Therapeutics," Poster, Keystone Symposium, Jan. 16, 2010, Keystone, Colorado, 1 page.
Marcusson, "Targeting microRNAs for Therapeutics," Presentation, 6th Annual Meeting of the OTS, Oct. 23, 2010, 24 pages.
Trang et al., "Systemic Delivery of Tumor Suppressor microRNA Mimics Using a Neutral Lipid Emulsion Inhibits Lung Tumors in Mice," Amer Soc Gene Cell Ther, 2011, 19(6):1116-1122.
Akinc et al., "A combinatorial library of lipid-like materials for delivery of RNAi therapeutics." Nature Biotechnology. (2008): 1-9.
Calin et al., "Human microRNA genes are frequently locacted at fragile sites and genomic regions involoved in cance. " PNAS 101.9 (2004): 2999-3004.
Chang et al., "Transactivation of miR-34a by p53 broadly influences geneexpression and promotes apoptosis. " Molecular Cell. 26.5 (2007): 745-752
Chang et al., "Widespread microRNA repression by Myc contributes to tumorigenesis. " Nature Genetics. 40.1 (2008): 43-50.
He et al., "A microRNA component of the p53 tumour suppressor network. "Nature. 447.28 (2007): 1130-1135
Hermeking, H. "p53 enters the microRNA world." Cancer Cel. 12.5 (2007): 414-418.
Kelnar et al. "Quantifications of Therapeutic miRNA Mimics in Whole Blood from Nonhuman Primates. " Anal. Chem. 86. (2014): 1534-1542.
Lim et al., "Vertebrate MicroRNA Genes. " Science 299 (2003): 1540.
Marcusson, "Therapeutic Targeting of MicroRNA, " Presented at MicroRNA and Cancer, Keystone Conference, Jun. 12, 2009, 34 pages.
Marcusson, "microRNA Based Therapeutics for Cancer, " Presented at Drug Discovery Summit, Oct. 16, 2009, 6 pages.
Marcusson et al., "microRNA Mimics As Cancer Therapeutics, " Keystone Conference Poster, Mar. 25, 2010, 1 page.
Marcusson et al., "microRNA Mimics As Cancer Therapeutics, "AACR poster, Apr. 20, 2010, 1 page.
Raver-Shapira et al., "Transcriptional activation of miR-34a contributes to p53-mediated apoptosis. "Molecular Cell. 26. (2007): 731-743.
Regulus Therapeutics, "Regulus Therapeutics Present New Pre-clinical Data from Multiple Therapeutic Programs at Keystone Symposium, "Press Releasee, Jan. 15, 2010, 2 pages.
International Search Report and Written Opinion mailed Apr. 14, 2011, for Application No. PCT/US2011/021287, filed Jan. 14, 2011, 11 pages.
Bader, "miR-34—A microRNA replacement therapy is headed to the clinic," Frontiers in Genetics, 2012, vol. 3, article 120, 9 pages.
Chen et al., "Nanoparticles modified with tumor-targeting scFv deliver siRNA and miRNA for cancer therapy," Mol Ther., 2010, 18:1650-1656.
Wiggins et al., "Development of a lung cancer therapeutic based on the tumor suppressor microRNA-34," Cancer Res., 2010, 70:5923-5930.

Circulating human aFP levels increased with time in animals with established orthotopic liver tumors.

Treatment with miR-34a-L09 led to down-regulation of multiple miR-34 targets in liver tumors.

Inhibition of liver tumor growth following replacement of miR-34a.

SEQUENCE LISTING

```
<160> NUMBER OF SEQ ID NOS: 9

<210> SEQ ID NO 1
<211> LENGTH: 22
<212> TYPE: RNA
<213> ORGANISM: Homo sapiens

<400> SEQUENCE: 1
uggcaguguc uuagcugguu gu                                              22

<210> SEQ ID NO 2
<211> LENGTH: 22
<212> TYPE: RNA
<213> ORGANISM: Homo sapiens

<400> SEQUENCE: 2
caaucacuaa cuccacugcc au                                              22

<210> SEQ ID NO 3
<211> LENGTH: 23
<212> TYPE: RNA
<213> ORGANISM: Homo sapiens

<400> SEQUENCE: 3
aggcagugua guuagcugau ugc                                             23

<210> SEQ ID NO 4
<211> LENGTH: 110
<212> TYPE: RNA
<213> ORGANISM: Homo sapiens

<400> SEQUENCE: 4
ggccagcugu gaguguuucu uuggcagugu cuuagcuggu uguugugagc aauaguaagg     60
aagcaaucag caaguauacu gcccuagaag ugcugcacgu uguggggccc               110

<210> SEQ ID NO 5
<211> LENGTH: 84
<212> TYPE: RNA
<213> ORGANISM: Homo sapiens

<400> SEQUENCE: 5
gugcucgguu uguaggcagu gucauuagcu gauuguacug uggugguuac aaucacuaac     60
uccacugcca ucaaaacaag gcac                                            84

<210> SEQ ID NO 6
<211> LENGTH: 77
<212> TYPE: RNA
<213> ORGANISM: Homo sapiens

<400> SEQUENCE: 6
agucuaguua cuaggcagug uaguuagcug auugcuaaua guaccaauca cuaaccacac     60
ggccagguaa aaagauu                                                    77

<210> SEQ ID NO 7
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 7
aaccagcuaa gacacugcca aa                                              22
```

```
<210> SEQ ID NO 8
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 8
ugcgaguguc uuagcugguu gu                                              22

<210> SEQ ID NO 9
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 9
aaacgcucac agaaucgacc aa                                              22
```

MICRORNA COMPOSITIONS AND METHODS

This application is a national stage of International Application No. PCT/US2011/021287, filed Jan. 14, 2011, which claims priority to U.S. Provisional Application No. 61/295,121, filed Jan. 14, 2010; U.S. Provisional Application No. 61/317,126, filed Mar. 24, 2010; and U.S. Provisional Application No. 61/325,747, filed Apr. 19, 2010; each of which is incorporated by reference herein in its entirety for any purpose.

FIELD OF INVENTION

Provided herein are compositions comprising miRNA mimics, and methods for their use in the treatment of cancer.

DESCRIPTION OF ART

MicroRNAs (miRNAs), also known as "mature miRNA" are small (approximately 18-24 nucleotides in length), non-coding RNA molecules encoded in the genomes of plants and animals. In certain instances, highly conserved, endogenously expressed miRNAs regulate the expression of genes by binding to the 3'-untranslated regions (3'-UTR) of specific mRNAs. More than 1000 different miRNAs have been identified in plants and animals. Certain mature miRNAs appear to originate from long endogenous primary miRNA transcripts (also known as pri-miRNAs, pri-mirs, pri-miRs or pri-pre-miRNAs) that are often hundreds of nucleotides in length (Lee, et al., EMBO J., 2002, 21(17), 4663-4670).

Functional analyses of miRNAs have revealed that these small non-coding RNAs contribute to different physiological processes in animals, including developmental timing, organogenesis, differentiation, patterning, embryogenesis, growth control and programmed cell death. Examples of particular processes in which miRNAs participate include stem cell differentiation, neurogenesis, angiogenesis, hematopoiesis, and exocytosis (reviewed by Alvarez-Garcia and Miska, Development, 2005, 132, 4653-4662). In some instances, miRNAs are thought to exercise post-transcriptional control in most eukaryotic organisms and have been detected in plants and animals as well as certain viruses.

Families of miRNAs can be characterized by nucleotide identity at positions 2-8 of the miRNA, a region known as the seed sequence. Lewis et al. describe several miRNA families, as well as miRNA superfamilies, which are characterized by related seed sequences (Lewis et al. Cell. 2005, 120(1): 15-20).

SUMMARY OF INVENTION

Provided herein are compositions that mimic miRNA activity. In certain embodiments, the compositions comprise oligomeric compounds comprising oligonucleotides having nucleobase sequence identity to a miRNA. In certain embodiments, the nucleobase sequence of an oligonucleotide having identity to a miRNA comprises a seed region of the miRNA. The miRNA may be miR-34. In certain embodiments, the miR-34 is miR-34a. The compositions may comprise one or more lipids. In certain embodiments, the one or more lipids is selected from a cationic lipid, a neutral lipid, a sterol, and a disaggregation lipid.

Also provided herein are methods for the treatment of cancer, comprising administering to a subject having cancer a composition comprising an oligomeric compound consisting of an oligonucleotide having nucleobase sequence identity to a miRNA. Such methods may, for example, comprise the administration of a composition comprising an oligomeric compound consisting of an oligonucleotide, wherein the oligonucleotide has nucleobase sequence identity to miR-34. The cancer may be any type of cancer, for example, liver cancer, breast cancer, lung cancer, colon cancer, ovarian cancer, cervical cancer, leukemia, lymphoma, brain cancer, esophageal cancer, Hodgkin lymphoma, non-Hodgkin lymphoma, kidney cancer, melanoma, myeloma, oral cancer, pancreatic cancer, prostate cancer, rectal cancer, stomach cancer, bladder cancer, thyroid cancer, or testicular cancer.

Provided herein are methods for treating cancer in a subject having a p53-expressing cancer comprising administering to a subject a composition comprising an oligomeric compound consisting of an oligonucleotide having nucelobase sequence identity to miR-34. In certain embodiments, the miR-34 is miR-34a.

Provided herein are methods for treating cancer in a subject having a p53-deficient cancer comprising administering to a subject a composition comprising an oligomeric compound consisting of an oligonucleotide having nucelobase sequence identity to miR-34. In certain embodiments, the miR-34 is miR-34a.

Provided herein are methods for treating cancer in a subject having a cancer comprising cells which overexpress an oncogene. In certain embodiments, the oncogene is Myc. Also provided herein are methods for treating cancer in a subject having a cancer comprising cells which have a Myc mutation.

Provided herein are compositions comprising an oligomeric compound comprising an oligonucleotide consisting of 7 to 30 linked nucleosides, wherein the nucleobase sequence of the oligonucleotide has at least 80% seed region identity with the nucleobase sequence of miR-34. In certain embodiments, the oligomeric compound consists of the oligonucleotide.

Provided herein are compositions comprising an oligomeric compound comprising an oligonucleotide hybridized to a complementary oligonucleotide, wherein the oligonucleotide has at least 80% seed region identity with the nucleobase sequence of miR-34 and the nucleobase sequence of the complementary oligonucleotide has at least 80% complementarity to the oligonucleotide. In certain embodiments, the oligomeric compound consists of the oligonucleotide hybridized to a complementary oligonucleotide.

In certain embodiments, the nucleoobase sequence of the oligonucleotide has at least 85%, at least 90%, or at least 95% seed region identity with the nucleobase sequence of miR-34. In certain embodiments, the nucleobase sequence of the oligonucleotide has 100% seed region identity with the nucleobase sequence of miR-34. In certain embodiments, the oligonucleotide has at least 70%, at least 75%, at least 80%, at least 90%, or at least 95% overall identity with the nucleobase sequence of miR-34. In certain embodiments, the oligonucleotide has 100% overall identity with the nucleobase sequence of miR-34.

In certain embodiments, the seed region comprises nucleobases 3-6, or 2-7 of miR-34. In certain embodiments, the seed region is nucleobases 1-6, 2-7, 2-8, 2-9, or 3-8 of miR-34.

In certain embodiments, miR-34 is miR-34 a. In certain embodiments, the miR-34a comprises SEQ ID NO: 1 (UGGCAGUGUCUUAGCUGGUUGU). In certain embodiments, the miR-34a consists of SEQ ID NO: 1 (UGGCAGUGUCUUAGCUGGUUGU). In certain embodiments, the miR-34 is miR-34c. In certain embodiments, the miR-34c comprises SEQ ID NO: 2 (AGGCAGUGUAG- UUAGCUGAUUGC). In certain embodiments, the miR-34c consists of SEQ ID NO: 2 (AGGCAGUGUAG-UUAGCUGAUUGC).

In certain embodiments, the oligonucleotide comprises at least one modified sugar or comprises a plurality of modified sugars. In certain embodiments, each nucleoside of the oligonucleotide comprises a modified sugar. In certain embodiments, the complementary oligonucleotide comprises at least one modified sugar or comprises a plurality of modified sugars. In certain embodiments, each nucleoside of the complementary oligonucleotide comprises a modified sugar. In certain embodiments, the modified sugar is independently selected from 2'-O-methyl, 2'-O-methoxyethyl, 2'-fluoro, and a bicyclic sugar.

In certain embodiments, the oligonucleotide comprises at least one modified internucleoside linkage. In certain embodiments, the oligonucleotide comprises a plurality of modified internucleoside linkages. In certain embodiments, the complementary oligonucleotide comprises at least one modified internucleoside linkage. In certain embodiments, the complementary oligonucleotide comprises a plurality of modified internucleoside linkages. In certain embodiments, each internucleoside linkage is a modified internucleoside linkage. In certain embodiments, the modified internucleoside linkage is phosphorothioate.

In certain embodiments, the oligonucleotide comprises at least one modified nucleobase. In certain embodiments, the complementary oligonucleotide comprises at least one modified nucleobase. In certain embodiments, the modified nucleobase is a 5-methylcytosine.

Provided herein are compositions comprising an oligomeric compound comprising an oligonucleotide consisting of 7 to 30 linked nucleosides, wherein the nucleobase sequence of the oligonucleotide has at least 80% seed region identity with the nucleobase sequence of miR-34, and at least one, at least two, at least three, or at least four lipids. In certain embodiments, a lipid is a cationic lipid. In certain embodiments, a lipid is an amino lipid. In certain embodiments, a lipid is a sterol. In certain embodiments, a lipid is a disaggregation lipid. In certain embodiments, a lipid is a neutral lipid. In certain embodiments, each lipid is selected from among a cationic lipid, a neutral lipid, a sterol, and a disaggregation lipid. In certain embodiments, the cationic lipid is 2,2-Dilinoleyl-4-dimethylaminoethyl-[1,3]-dioxolane. In certain embodiments, the sterol is cholesterol. In certain embodiments, the disaggregation lipid is a polyethylene glycol lipid (PEG-Lipid). In certain embodiments, the PEG-lipid is PEG-didimyristoyl glycerol (PEG-DMG). In certain embodiments, the PEG-lipid is PEG-distyryl glycerol (PEG-DSG). In certain embodiments, the PEG-lipid is PEG-carbamoyl-1,2-dimyristyloxypropylamine (PEG-cDMA). In certain embodiments, the lipid is a phospholipid. In certain embodiments, the phospholipid is phosphatidylcholine. In certain embodiments, the phosphatidylcholine is distearoylphosphatidylcholine. In certain embodiments, the phosphatidylcholine is dipalmitoylphosphatidylcholine. In certain embodiments, the composition comprises a cationic lipid, neutral lipid, sterol, and disaggregation lipid in a molar ratio of 50 to 60:7 to 10:30 to 40:1 to 5. In certain embodiments, the molar ratio is 57.5:7.5:31.5:3.5; 60:7.5:31:1.5; or 50:10:38.5:1.5.

In certain embodiments, the lipid:oligomeric compound ratio is from 5 to 35 or from 5 to 15. In certain embodiments, the lipid:oligomeric compound ratio is 6; 7; 8; 9; 10; or 11.

Any of the compositions provided herein may comprise a pharmaceutically acceptable carrier or diluent.

Provided herein are methods for treating cancer, comprising administering to a subject having cancer a composition provided herein. The cancer may be liver cancer, breast cancer, lung cancer, colon cancer, ovarian cancer, cervical cancer, leukemia, lymphoma, brain cancer, esophageal cancer, Hodgkin lymphoma, non-Hodgkin lymphoma, kidney cancer, melanoma, myeloma, oral cancer, pancreatic cancer, prostate cancer, rectal cancer, stomach cancer, bladder cancer, thyroid cancer, and testicular cancer. The liver cancer may be hepatocellular carcinoma. The liver cancer may comprise secondary liver cancer, which may be the result of colorectal cancer with metastasis to the liver. The subject may be a human. The route of administration may comprise intravenous administration, subcutaneous administration, intratumoral administration, or chemoembolization.

In certain embodiments, the methods provided herein comprise at least one additional therapy. The at least one additional therapy may comprise a chemotherapeutic agent and/or radiation therapy. The chemotherapeutic agent may be selected from 5-fluorouracil, gemcitabine, doxorubicine, mitomycin c, sorafenib, etoposide, carboplatin, epirubicin, irinotecan and oxaliplatin. The at least one additional therapy may be administered at the same time, less frequently, or more frequently than administration of a composition provided herein.

In any of the methods provided herein, the composition may be administered once per day, once per week, once per two weeks, once per three weeks, or once per four weeks.

In any of the methods provided herein, administering results in reduction of tumor size, and/or reduction of tumor number. In any of the methods provided herein, the administering prevents an increase in tumor size and/or an increase in tumor number. The administering may prevent, stop or slow metastatic progression. The administering may extend the overall survival time of the subject. The administering may extend progression-free survival of the subject.

In certain embodiments, the methods provided herein comprise selecting a subject having liver lesions. In certain embodiments, the subject has elevated serum alpha-fetoprotein or elevated serum des-gamma-carboxyprothrombin. In certain embodiments, the administering reduces serum alpha-fetoprotein or serum des-gamma-carboxyprothrombin. In certain embodiments, a subject has abnormal liver function. In certain embodiments, the administering prevents a worsening or improves liver function in the subject.

The subject may have a p53-deficient cancer. The subject may have a p53-expressing cancer. The methods provided herein may comprise selecting either such subject.

Provided herein are methods of regulating seed-matched transcripts comprising contacting a cell with any of the compositions provided herein. In certain embodiments, seed-matched transcript are down-regulated. In certain embodiments, the seed-matched transcripts comprise cell cycle genes. In certain embodiments, apoptosis is induced in the cell. In certain embodiments, senescence is induced in the cell. In certain embodiments, cell cycle arrest is induced in the cell. In certain embodiments, the cell is a cancer cell. In certain embodiments, the cancer cell is a liver cancer cell. In certain embodiments, the cancer cell is a p-53 deficient cancer cell. In certain embodiments, the cancer cell is a p-53 expressing cancer cell. The cancer cells may have a Myc mutation. The cancer cells may comprise overexpressed Myc.

In any of the methods provided herein, the cancer comprises cells which overexpress an oncogen. In certain embodiments, the oncogene is Myc. In certain embodiments, the cancer comprises cells which have a Myc mutation.

The present invention also provides for any of the compounds described herein for use as a medicament. The present invention also provides for any of the compounds described herein for preventing, treating, or diagnosing any of the diseases or conditions described herein. The present invention also provides for use of any of the compounds described herein for preventing, treating, or diagnosing any of the diseases or conditions described herein.

These and other embodiments of the present invention will become apparent in conjunction with the figures, description and claims that follow.

DETAILED DESCRIPTION

Figure 1:
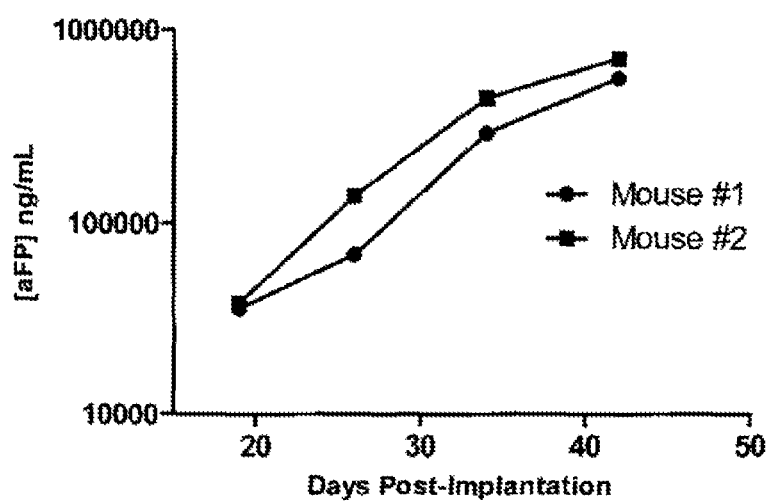
FIG. 1: Circulating human aFP levels increased with time in animals with established orthotopic liver tumors. aFP levels were measured 19, 26, 34 and 42 days after establishment of orthotopic tumors.

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can command go, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

DEFINITIONS

"Liver cancer" means cancer present in the liver, either a primary liver cancer or a secondary liver cancer. In certain embodiments, liver cancer includes, but is not limited to, cancer arising from hepatocytes, such as, for example, hepatomas and hepatocellular carcinomas; fibrolamellar carcinoma; and cholangiocarcinomas (or bile duct cancer). In certain embodiments, liver cancer includes, but is not limited to, secondary cancer that originated as colorectal cancer and metastasized to the liver.

"Hepatocellular carcinoma" means primary cancer of the liver arising from hepatocytes.

"p53-deficient cancer" means a cancer characterized by reduced or absent expression of p53 mRNA and/or protein.

"p53-expressing cancer" means a cancer characterized by expression of p53 mRNA and/or protein.

"Myc mutation" means a change in the Myc DNA sequence. In certain embodiments, the Myc mutation is a chromosomal translocation. In certain embodiments, the Myc mutation is a point mutation. In certain embodiments, aberrant expression is overexpression. "Primary liver cancer" means a cancer that originates in the liver. For example, primary liver cancers include, but are not limited to, hepatoma, hepatocellular carcinoma, fibromellar carcinoma, and cholangiocarcinoma.

"Secondary liver cancer" means a cancer that is present in the liver, but originated elsewhere in the body. For example, cancer may originate as colorectal cancer, and the colorectal cancer cells may metastasize to the liver to form liver cancer of colorectal origin. Secondary liver cancer may originate as cancer including, but not limited to, breast cancer, lung cancer, colorectal cancer, and brain cancer.

"Subject" means a human or non-human animal selected for treatment or therapy.

"Subject in need thereof" means a subject identified as in need of a therapy or treatment. In certain embodiments, a subject has liver cancer. In such embodiments, a subject has one or more clinical indications of liver cancer or is at risk for developing liver cancer.

"At risk for developing cancer" means the state in which a subject is predisposed to developing cancer.

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects need only be overlapping for a period of time and need not be coextensive.

"Chemoembolization" means a procedure in which the blood supply to a tumor is blocked surgically, mechanically, or chemically and chemotherapeutic agents are administered directly into the tumor.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, surgical resection, liver transplant, and/or chemoembolization.

"Treatment" means the application of one or more specific procedures used for the cure or amelioration of a disease. In certain embodiments, the specific procedure is the administration of one or more pharmaceutical agents.

"Amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Prevention" refers to delaying or forestalling the onset or development or progression of a condition or disease for a period of time, including weeks, months, or years.

"Prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Anti-cancer therapy" means a therapy aimed at treating or preventing cancer. In certain embodiments, anti-cancer therapy comprises chemotherapy. In certain embodiments, anti-cancer therapy comprises radiation therapy.

"Chemotherapeutic agent" means a pharmaceutical agent used to treat cancer.

"Chemotherapy" means treatment of a subject with one or more pharmaceutical agents for the treatment of cancer.

"Radiation therapy" means administration of ionizing radiation to eliminate, reduce, and/or slow the growth of cancer cells.

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

"Overall survival time" means the time period for which a subject survives after diagnosis of or treatment for a disease. In certain embodiments, the disease is cancer.

"Progression-free survival" means the time period for which a subject having a disease survives, without the disease getting worse. In certain embodiments, progression-free survival is assessed by staging or scoring the disease. In certain embodiments, progression-free survival of a subject having liver cancer is assessed by evaluating tumor size, tumor number, and/or metastasis.

"Biomarker" means a substance that is used as an indicator of a biologic state. Biomarkers are objectively measured and evaluated as an indicator of normal biologic processes, pathogenic processes, or pharmacologic responses to a therapeutic intervention.

"Cancer biomarker" means a substance that is used as an indicator of a cancerous state. For example, a cancer biomarker may indicate the presence of cancer, or the response to an anti-cancer therapy.

"Improved liver function" means the change in liver function toward normal liver function. In certain embodiments, liver function is assessed by measuring molecules found in a subject's blood. For example, in certain embodiments, improved liver function is measured by a reduction in blood liver transaminase levels.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise an oligonucleotide and a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Injection site reaction" means inflammation or abnormal redness of skin at a site of injection in an individual.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

"Target nucleic acid," "target RNA," "target RNA transcript" and "nucleic acid target" all mean any nucleic acid capable of being targeted by antisense compounds.

"Targeting" means the process of design and selection of nucleobase sequence that will hybridize to a target nucleic acid and induce a desired effect.

"Targeted to" means having a nucleobase sequence that will allow hybridization to a target nucleic acid to induce a desired effect. In certain embodiments, a desired effect is reduction of a target nucleic acid.

"Target engagement" means the interaction of a drug with its target molecule in a manner that changes the activity, expression or level of the target. In certain embodiments, target engagement means a miRNA interacting with its target transcripts, such that the expression or level of the transcript is decreased in an miRNA-dependent manner.

"Modulation" means to a perturbation of function or activity. In certain embodiments, modulation means an increase in activity. In certain embodiments, modulation means a decrease in activity.

"Expression" means any functions and steps by which a gene's coded information is converted into structures present and operating in a cell.

"5' target site" refers to the nucleobase of a target nucleic acid which is complementary to the 5'-most nucleobase of a particular oligonucleotide.

"3' target site" means the nucleobase of a target nucleic acid which is complementary to the 3'-most nucleobase of a particular oligonucleotide.

"Region" means a portion of linked nucleosides within a nucleic acid. In certain embodiments, an oligonucleotide has a nucleobase sequence that is complementary to a region of a target nucleic acid. For example, in certain such embodiments an oligonucleotide is complementary to a region of a miRNA stem-loop sequence. In certain such embodiments, an oligonucleotide is fully complementary to a region of a miRNA stem-loop sequence.

"Segment" means a smaller or sub-portion of a region.

"Nucleobase sequence" means the order of contiguous nucleobases, in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that an oligomeric compound is capable of hybrizing to a target nucleic acid under stringent hybridization conditions.

"Complementarity" means the nucleobase pairing ability between a first nucleic acid and a second nucleic acid.

"Fully complementary" means each nucleobase of an oligomeric compound is capable of pairing with a nucleobase at each corresponding position in a target nucleic acid. For example, in certain embodiments, an oligomeric compound wherein each nucleobase has complementarity to a nucleobase within a region of a miRNA stem-loop sequence is fully complementary to the miRNA stem-loop sequence.

"Percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound. In certain embodiments, percent complementarity of an means the number of nucleobases that are complementary to the target nucleic acid, divided by the length of the modified oligonucleotide.

"Overall identity" means the number of nucleobases in a first oligomeric compound that are identical to nucleobases at corresponding positions in a second oligomeric compound, divided by the total number of nucleobases in the first oligomeric compound.

"Region identity" means the number of nucleobases in a region of a first oligomeric compound that are identical to nucleobases at corresponding positions in a second oligomeric compound, divided by the number of nucleobases in the region.

"Central complementary region" means a region of complementarity between a first oligonucleotide and a second oligonucleotide, where the hybridization of the first and second oligonucleotide results in the formation of one or more overhangs.

"Seed region identity" means the nucleobase sequence identity between the nucleobase sequence of a seed region and contiguous nucleobases of an oligomeric compound. "Seed region identity" can also be referred to as "seed sequence identity."

"Nucleobase identity" means nucleobases that are the same as one another.

"Nucleobase sequence identity" means nucleobase sequences that are at least partially the same as one another. Nucleobase sequence identity may be less than 100%.

"Hybridize" means the annealing of complementary nucleic acids that occurs through nucleobase complementarity.

"Mismatch" means a nucleobase of a first nucleic acid that is not capable of pairing with a nucleobase at a corresponding position of a second nucleic acid.

"Non-identical nucleobase" means nucleobases that are different from one another.

"Non-complementary nucleobase" means two nucleobases that are not capable of pairing through hydrogen bonding.

"MicroRNA" means an endogenous non-coding RNA between 18 and 25 nucleobases in length, which is the product of cleavage of a pre-miRNA by the enzyme Dicer. Examples of mature miRNAs are found in the miRNA database known as miRBase (available on the world wide web at "microrna.sanger.ac.uk/"). In certain embodiments, microRNA is abbreviated as "miRNA" or "miR."

"Pre-miRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature miRNA sequence. Pre-miRNA sequences and stem-loop sequences may overlap. Examples of stem-loop sequences are found in the miRNA database known as miRBase (available at the world wide web at "microrna.sanger.ac.uk/").

"Pri-miRNA" or "pri-miR" means a non-coding RNA having a hairpin structure that is a substrate for the double-stranded RNA-specific ribonuclease Drosha.

"miRNA precursor" means a transcript that originates from a genomic DNA and that comprises a non-coding, structured RNA comprising one or more miRNA sequences. For example, in certain embodiments a miRNA precursor is a pre-miRNA. In certain embodiments, a miRNA precursor is a pri-miRNA.

"miR-34 family" means miR-34 microRNA or microRNA precursors that share a seed sequence. In certain embodiments, the miR-34 family includes miR-34a, miR-34b, and miR-34c.

"miR-34" means a mature microRNA that is a member of the miR-34 family.

"miR-34a" means the mature miRNA having the nucleobase sequence of SEQ ID NO: 1 (UGGCAGUGUCUUAGCUGGUUGU).

"miR-34b" means the mature miRNA having the nucleobase sequence of SEQ ID NO: 2 (CAAUCACUAACUCCACUGCCAU).

"miR-34c" means the mature miRNA having the nucleobase sequence of SEQ ID NO: 3 (AGGCAGUGUAGUUAGCUGAUUGC).

"Mimic" means an oligomeric compound comprising an oligonucleotide having nucleobase sequence identity to a mature.

"miR-34 mimic" means an oligomeric compound comprising an oligonucleotide having nucleobase sequence identity to miR-34.

"Monocistronic transcript" means a miRNA precursor containing a single miRNA sequence.

"Polycistronic transcript" means a miRNA precursor containing two or more miRNA sequences.

"Seed sequence" or "seed region" means a nucleobase sequence comprising from 6 to 8 contiguous nucleobases of nucleobases 1 to 8 of the 5'-end of a mature microRNA sequence.

"Seed sequence" and "seed region" can be used interchangeably and refer to the same sequence as it is defined for the term "seed sequence."

"Seed match sequence" means a nucleobase sequence that is complementary to a seed sequence, and is the same length as the seed sequence.

"Seed-matched transcript" means a transcript that contains a nucleobase sequence to which a seed sequence is complementary. In certain embodiments, the expression of a seed-matched transcript is regulated by a microRNA comprising the seed sequence that is complementary to the seed-matched transcript.

"Oligomeric compound" means a compound comprising a polymer of linked monomeric subunits. In certain embodiments, an oligomeric compound is a single-stranded oligomeric compound. In certain embodiments, an oligomeric compound is a double-stranded oligomeric compound.

"Oligonucleotide" means a polymer of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2'-H) or RNA (2'-OH).

"Natural nucleobase" means a nucleobase that is unmodified relative to its naturally occurring form.

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar.

"Nucleotide" means a nucleoside having a phosphate group covalently linked to the sugar portion of a nucleoside.

"Modified oligonucleotide" means an oligonucleotide having one or more modifications relative to a naturally occurring terminus, sugar, nucleobase, and/or internucleoside linkage.

"Single-stranded modified oligonucleotide" means a modified oligonucleotide which is not hybridized to a complementary strand.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar" means substitution and/or any change from a natural sugar.

"Modified nucleobase" means any substitution and/or change from a natural nucleobase.

"5-methylcytosine" means a cytosine modified with a methyl group attached to the 5' position.

"2'-O-methyl sugar" or "2'-OMe sugar" means a sugar having a O-methyl modification at the 2' position.

"2'-O-methoxyethyl sugar" or "2'-MOE sugar" means a sugar having a O-methoxyethyl modification at the 2' position.

"2'-O-fluoro" or "2'-F" means a sugar having a fluoro modification of the 2' position.

"Bicyclic sugar moiety" means a sugar modified by the bridging of two non-geminal ring atoms.

"2'-O-methoxyethyl nucleoside" means a 2'-modified nucleoside having a 2'-O-methoxyethyl sugar modification.

"2'-fluoro nucleoside" means a 2'-modified nucleoside having a 2'-fluoro sugar modification.

"2'-O-methyl" nucleoside means a 2'-modified nucleoside having a 2'-O-methyl sugar modification.

"Bicyclic nucleoside" means a 2'-modified nucleoside having a bicyclic sugar moiety.

"Motif" means a pattern of modified and/or unmodified nucleobases, sugars, and/or internucleoside linkages in an oligonucleotide.

A "fully modified oligonucleotide" means each nucleobase, each sugar, and/or each internucleoside linkage is modified.

A "uniformly modified oligonucleotide" means each nucleobase, each sugar, and/or each internucleoside linkage has the same modification throughout the modified oligonucleotide.

A "gapmer" means a modified oligonucleotide having an internal region of linked nucleosides positioned between two external regions of linked nucleosides, where the nucleosides of the internal region comprise a sugar moiety different than that of the nucleosides of each external region.

A "gap segment" is an internal region of a gapmer that is positioned between the external regions.

A "wing segment" is an external region of a gapmer that is located at the 5' or 3' terminus of the internal region.

A "symmetric gapmer" means each nucleoside of each external region comprises the same sugar modification.

An "asymmetric gapmer" means each nucleoside of one external region comprises a first sugar modification, and each nucleoside of the other external region comprises a second sugar modification.

A "stabilizing modification" means a modification to a nucleoside that provides enhanced stability to a modified oligonucleotide, in the presence of nucleases, relative to that provided by 2'-deoxynucleosides linked by phosphodiester internucleoside linkages. For example, in certain embodiments, a stabilizing modification is a stabilizing nucleoside modification. In certain embodiments, a stabilizing modification is a internucleoside linkage modification.

A "stabilizing nucleoside" means a nucleoside modified to provide enhanced nuclease stability to an oligonucleotide, relative to that provided by a 2'-deoxynucleoside. In one embodiment, a stabilizing nucleoside is a 2'-modified nucleoside.

A "stabilizing internucleoside linkage" means an internucleoside linkage that provides enhanced nuclease stability to an oligonucleotide relative to that provided by a phosphodiester internucleoside linkage. In one embodiment, a stabilizing internucleoside linkage is a phosphorothioate internucleoside linkage.

Overview

Certain changes in miRNA expression patterns in cancer cells relative to non-cancerous cells have been reported. Both increases and decreases in miRNA expression have been described in relation to cancer. Accordingly, there exists a need for compositions and methods for the treatment of cancers characterized by disregulation of miRNA expression.

As cancer is a disease caused by the uncontrolled proliferation of cells, as well as increased cell survival, desirable traits of pharmaceutical agents for the treatment of liver cancer include the ability to reduce cell proliferation, and/or induce apoptosis, which will in turn reduce tumor size, reduce tumor number, and/or prevent or slow the metastasis of liver cancer cells.

It is demonstrated herein that compositions comprising a miR-34 mimic can be efficiently delivered to tumors, and result in the specific down-regulation of transcripts containing miR-34 seed matches. Certain of the down-regulated targets were genes having cell cycle and mitotic functions, indicating an effect on transcripts that regulate cell cycle and proliferation. It is further demonstrated herein that delivery of a miR-34 mimic to a tumor results in inhibition of tumor growth.

Accordingly, provided herein are compositions and methods for the treatment of cancer. These methods may result in one or more clinically desirable outcomes in a subject having cancer, such as reduction in tumor number and/or size, reduced metastatic progression, prolonged survival time, and/or increased progression-free survival time. Also provided herein are pharmaceutical compositions that may be used for the treatment of cancer.

Having the information disclosed herein, one of ordinary skill in the art would comprehend that of other classes of compounds mimicking miRNAs, for example miR-34, such as antibodies, small molecules, and peptides, can be assessed for their effects on the physiological indicators of cancer in in vivo models, and these compounds can be developed for the treatment, amelioration or prevention of cancer. Such compounds are envisioned as within the scope of the instant invention.

Certain Conditions and Treatments

In certain embodiments, the present invention provides methods for the treatment of cancer comprising administering to a subject having cancer a composition comprising an oligomeric compound comprising an oligonucleotide having nucleobase identity to miR-34.

A subject may be diagnosed with cancer following the administration of medical tests well-known to those in the medical profession. In certain embodiments, the cancer is detected following a computed tomography (CT) scan that detects tumors. In certain embodiments, the cancer is detected following magnetic resonance imaging (MRI). In certain embodiments, cancer is characterized as a single primary tumor. In certain embodiments, cancer is characterized as multiple primary tumors. In certain embodiments, cancer is characterized as a poorly defined primary tumor with an infiltrative growth pattern. In certain embodiments, the cancer is a single primary tumor with vascular invasion. In certain embodiments, the cancer is characterized as multiple primary tumors with vascular invasion. In certain embodiments, the cancer has metastasized to one or more lymph nodes. In certain such embodiments, the lymph nodes are regional lymph nodes. In certain embodiments, the cancer has metastasized to one or more distant tissues. In certain embodiments, the cancer has metastasized to the liver, the portal vein, lymph nodes, adrenal glands, bone or lungs.

In certain embodiments, the cancer is liver cancer, breast cancer, lung cancer, colon cancer, ovarian cancer, cervical cancer, leukemia, lymphoma, brain cancer, esophageal cancer, Hodgkin lymphoma, non-Hodgkin lymphoma, kidney cancer, melanoma, myeloma, oral cancer, pancreatic cancer, prostate cancer, rectal cancer, stomach cancer, bladder cancer, thyroid cancer, or testicular cancer.

A subject's response to treatment may be evaluated by tests similar to those used to diagnosis the liver cancer, including, without limitation, CT scan, MRI, and needle biopsy. Response to treatment may also be assessed by measuring biomarkers in blood, for comparison to pre-treatment levels of biomarkers.

Administration of a composition of the present invention to a subject having cancer may result in one or more clinically desirable outcomes. Such clinically desirable outcomes include reduction of tumor number, reduction of tumor size and/or reduction of a cancer biomarker. Additional clinically desirable outcomes include the extension of overall survival time of the subject, and/or extension of progression-free survival time of the subject. In certain embodiments, administration of a composition of the invention prevents an increase in tumor size and/or tumor number. In certain embodiments, administration of a composition of the invention prevents metastatic progression. In certain embodiments, administration of a composition of the invention slows or stops metastatic progression. In certain embodiments, administration of a composition of the invention prevents the recurrence of tumors. In certain embodiments, administration of a composition of the invention prevents recurrence of metastasis of a tumor derived from any type of cancer.

Administration of a composition of the present invention to cancer cells may result in desirable phenotypic effects. In certain embodiments, a composition of the invention may stop, slow or reduce the uncontrolled proliferation of cancer cells. In certain embodiments, a composition of the invention may induce apoptosis in cancer cells. In certain embodiments, a composition of the invention may induce senescence in cancer cells. In certain embodiments, a composition of the invention may reduce cancer cell survival.

A miRNA hybridizes to one or more mRNAs to regulate expression of the mRNA and its protein product. Generally, the hybridization of a miRNA to its mRNA target down-regulates a mRNA transcript. Thus, the contacting of a cell with a miRNA mimic may result in the down-regulation of one or more miRNA nucleic acid targets.

A subject may have a cancer characterized by the reduced or absent expression of one or more tumor suppressors. For example, miR-34 acts in a regulatory loop with the tumor suppressor p53. Accordingly, in certain embodiments, a subject having cancer has a p53-deficient cancer. In certain embodiments, a subject have a p53-deficient cancer receives treatment with a composition comprising a miR-34 mimic and at least one additional therapy, wherein the at least on additional therapy is a compound that activates the p53 pathway. In certain embodiments, a compound that activates the p53 pathway is a small molecule compound, for example, a small molecule antagonist of MDM2.

In certain embodiments, a subject may have a cancer that is a p53-expressing cancer. In such cancers, the p53 tumor suppressor pathway is at least partly functional. Accordingly, provided herein are methods for administration of a composition comprising a miR-34 mimic to a subject having a p53-expressing cancer. In certain embodiments, such methods comprise selecting a subject having a p53-expressing cancer.

A subject may have a cancer characterized by the overexpression of one or more oncogenes. In certain embodiments, a subject having cancer has a cancer in which the Myc gene or protein is mutated. In certain embodiments, the Myc mutation is a translocation. In certain embodiments, a subject having cancer has a cancer in which the Myc gene or protein is overexpressed.

Liver Cancer

Liver cancer is a common cause of cancer deaths in both men and women worldwide. The incidence of hepatocellular carcinoma (HCC), the most common type of liver cancer, is rising. Certain HCC cases have been linked to chronic hepatitis B infection, chronic hepatitis C infection, or cirrhosis. Subjects with HCC have a very poor prognosis, with typical median survival from the date of diagnosis ranging from 7 to 8 months, and a 5 year survival rate of less than 5%. Limited treatments are available for HCC. Subjects with early stage disease may be treated by liver resection or liver transplantation. However, in approximately 85% of subjects the disease is too advanced at the time of diagnosis for liver resection or transplantation. Subjects with intermediate disease may be candidates for chemoembolization. However, the poor health of subjects with advanced disease limits the use of chemoembolization.

The diagnosis of hepatocellular carcinoma is typically made by liver imaging tests such as abdominal ultrasound, helical computed tomography (CT) scan or triple phase CT scan. Such imaging tests may be performed in conjunction with measurement of blood levels of alpha-fetoprotein and/or blood levels of des-gamma-carboxyprothrombin. In certain subjects, MRI may be used in place of CT scan. The liver imaging tests allow the assessment of the tumor size, number, location, metastasis outside the liver, patency and or invasion of the arteries and veins of the liver by the tumor. This assessment aids the decision as to the mode of therapeutic or palliative intervention that is appropriate. The final diagnosis is typically confirmed by needle biopsy and histopathological examination.

In certain embodiments, the cancer is liver cancer. In certain embodiments, the liver cancer is hepatocellular carcinoma (HCC). In certain embodiments, the liver cancer is a primary cancer which originated in the liver. Examples of primary liver cancer include, but are not limited to, hepatocellular carcinoma, cholangiocarcinomas, angiosarcomas, hemangiosarcomas, and hepatoblastoma.

In certain embodiments, the liver cancer is a metastatic cancer, originating in a tissue other than the liver. In certain embodiments, the metastatic cancer is breast cancer, colorectal cancer, or lung cancer. Treatments for metastatic liver cancer can comprise the same treatments used for primary liver cancer. In certain embodiments, a subject receiving treatment for metastatic liver cancer is also receiving treatment for the primary cancer from which the metastatic cancer originated.

In certain embodiments, the liver cancer is a p53-expressing cancer. In certain embodiments, the liver cancer is a p53-deficient cancer. In certain embodiments, a subject have a p53-deficient cancer receives treatment with a composition comprising a miR-34 mimic and at least one additional therapy, wherein the at least on additional therapy is a compound that activates the p53 pathway. In certain embodiments, a compound that activates the p53 pathway is a small molecule compound, for example, a small molecule antagonist of MDM2.

A number of systems have been employed to predict the prognosis for liver cancer, including the TNM system, the Okuda system, the Barcelona Clinic Liver Cancer (BCLC) and the CLIP score. Each of these systems incorporates four features that have been recognized as being important determinants of survival: the severity of underlying liver disease, the size of the tumor, extension of the tumor into adjacent structures, and the presence of metastases. The TNM system classifies HCC as stage I, II, III, IV, or V. The BCLC classifies HCC as Stage A1, A2, A3, A4, B, C, and D, and includes consideration of a Child-Pugh score.

In certain embodiments, liver cancer is classified as Stage 1, Stage 2, Stage 3A, Stage 3B, Stage 3C, or Stage 4. Stage 1 is characterized by a cancer is no bigger than 2 cm in size and that has not begun to spread. At Stage 2, the cancer is affecting blood vessels in the liver, or there is more than one tumor in the liver. At Stage 3A, the cancer is bigger than 5 cm in size or has spread to the blood vessels near the liver. At Stage 3B, the cancer has spread to nearby organs, such as the bowel or the stomach, but has not spread to the lymph nodes. At Stage 3C the cancer can be of any size and has spread to nearby lymph nodes. At Stage 4 the cancer has spread to parts of the body further away from the liver, such as the lungs.

Biomarkers in a subject's blood may be used to augment a diagnosis of liver cancer, stage a liver cancer, or develop a prognosis for survival. Such biomarkers include, but are not limited to, alpha-fetoprotein and des-gamma carboxyprothrombin. In certain embodiments, a subject having liver cancer has elevated blood alpha-fetoprotein. In certain embodiments, a subject having liver cancer has elevated blood des-gamma carboxyprothrombin.

A subject having liver cancer may also suffer from abnormal liver function. Liver function may be assessed by liver function tests, which measure, among other things, blood levels of liver transaminases. In certain embodiments, a subject having abnormal liver function has elevated blood liver transaminases. Blood liver transaminases include alanine aminotransferase (ALT) and aspartate aminotransferase (AST). In certain embodiments, a subject having abnormal liver function has elevated blood bilirubin. In certain embodiments, a subject has abnormal blood albumin levels.

In certain embodiments, a subject's liver function is assessed by the Child-Pugh classification system, which defines three classes of liver function. In this classification system, points are assigned to measurements in one of five categories: bilirubin levels, albumin levels, prothrombin time, ascites, and encephalopathy. One point is assigned per each of the following characteristics present: blood bilirubin of less than 2.0 mg/dl; blood albumin of greater than 3.5 mg/dl; a prothrombin time of less than 1.7 international normalized ratio (INR); ascites is absent; or encephalopathy is absent. Two points are assigned per each of the following characteristics present: blood bilirubin of 2-3 mg/dl; blood bilirubin of 3.5 to 2.8 mg/dl; prothrombin time of 1.7-2.3 INR; ascites is mild to moderate; or encephalopathy is mild. Three points are assigned per each of the following characteristics present: bilirubin of greater than 3.0 mg/dl; blood albumin of less than 2.8 mg/dl; prothrombin time of greater than 2.3 INR; ascites is severe to refractory; or encephalopathy is severe. The scores are added and Class A is assigned for a score of 5-6 points, Class B is assigned for a score of 7-9 points, and Class C assigned for a score of 10-15 points.

A subject having liver cancer may have or may have suffered from other conditions of the liver. In certain embodiments, a subject having liver cancer has or has suffered from chronic hepatitis C infection, chronic hepatitis B infection. In certain embodiments, a subject having liver cancer has or has suffered from cirrhosis. In certain embodiments, a subject having liver cancer has or has suffered from alcoholic fatty liver disease. In certain embodiments, a subject having liver cancer has or has suffered from non-alcoholic fatty liver disease (NAFLD). Subjects having liver cancer and any caused by hepatitis C infection, hepatitis B infection, or cirrhosis may be treated by the methods described herein.

Certain desirable clinical outcomes may be assessed by measurements of biomarkers. In certain embodiments, administration of a composition of the invention may result in the decrease of blood alpha-fetoprotein and/or blood des-gamma carboxyprothrombin. Administration of a composition of the invention may further result in the improvement of liver function, as evidenced by a reduction in blood ALT and/or AST levels.

Certain Compositions

Provided herein are compositions comprised of at least one lipid for use in delivering oligomeric compounds, including miRNA mimics, to cells and tissues. In certain embodiments, a lipid is selected to enhance the delivery of an oligomeric compound to a particular tissue, for example, the liver.

In certain embodiments, a composition comprises at least one lipid. In certain embodiments, a composition comprises at least two lipids. In certain embodiments, a composition comprises at least three lipids. In certain embodiments, a composition comprises at least four lipids.

In certain embodiments, a composition of the invention comprises a cationic lipid, a neutral lipid, a sterol, and a disaggregation lipid.

In certain embodiments, a cationic lipid is 2,2-Dilinoleyl-4-dimethylaminoethyl-[1,3]-dioxolane.

In certain embodiments, a sterol is cholesterol.

In certain embodiments, a disaggregation lipid is a polyethylene glycol-modified lipid (PEG-modified lipid). In certain embodiments a PEG-modified lipid is PEG-didimyristoyl glycerol (PEG-DMG). In certain embodiments a PEG-modified lipid is PEG-distyryl glycerol (PEG-DSG). In certain embodiments a PEG-modified lipid is PEG-carbamoyl-1,2-dimyristyloxypropylamine (PEG-cDMA).

In certain embodiments, a neutral lipid is a phospholipid. In certain embodiments, a phospholipid is selected from phosphatidylcholine (PC), distearoylphosphatidylcholine (DSPC), and dipalmitoylphosphatidylcholine (DPPC).

In certain embodiments, the composition consists of or consists essentially of a cationic lipid, a neutral lipid, cholesterol, and a PEG-modified lipid. In certain embodiments, a composition consists of or consists essentially of the above lipid mixture in molar ratios of about 20-70% cationic lipid: 5-45% neutral lipid:20-55% cholesterol:0.5-15% PEG-modified lipid. In certain embodiments, the composition comprises a cationic lipid, neutral lipid, sterol, and disaggregation lipid in a molar ratio of 50 to 60:7 to 10:30 to 40:1 to 5. In certain embodiments, the molar ratio is 57.5:7.5:31.5:3.5. In certain embodiments, the molar ratio is 60:7.5:31:1.5. In certain embodiments, the molar ratio is 50:10:38.5:1.5.

In certain embodiments, the ratio of total lipid to oligomeric compound is from 5 to 35 (i.e. from 5 to 1 to 35 to 1, lipid weight to oligomeric compound weight). In certain embodiments, the ratio of total lipid to oligomeric compound is from 5 to 15 (i.e. from 5 to 1 to 15 to 1, lipid weight to oligomeric compound weight). In certain embodiments, the ratio of total lipid to oligomeric compound is 5 (i.e. 5 to 1, lipid weight to compound weight). In certain embodiments, the ratio of total lipid to oligomeric compound is 6 (i.e. 6 to 1, lipid weight to compound weight). In certain embodiments, the ratio of total lipid to oligomeric compound is 7 (i.e. 7 to 1, lipid weight to compound weight). In certain embodiments, the ratio of total lipid to oligomeric compound is 8 (i.e. 8 to 1, lipid weight to compound weight). In certain embodiments, the ratio of total lipid to oligomeric compound is 9 (i.e. 9 to 1, lipid weight to compound weight). In certain embodiments, the ratio of total lipid to oligomeric compound is 10 (i.e. 10 to 1, lipid weight to compound weight). In certain embodiments, the ratio of total lipid to oligomeric compound is 11 (i.e. 11 to 1, lipid weight to compound weight).

In certain embodiments, a composition of the invention comprises an oligomeric compound, a cationic lipid, a neutral lipid, a sterol, and a disaggregation lipid in a molar ratio of 57.5 to 7.5 to 31.5 to 3.5 wherein the cationic lipid is 2,2-Dilinoleyl-4-dimethylaminoethyl-[1,3]-dioxolane (XTC), the neutral lipid is distearoylphosphatidylcholine (DSPC), the sterol is cholesterol and the disaggregation lipid is PEG-didimyristoyl glycerol (PEG-DMG), and wherein the ratio of total lipid to oligomeric compound ratio is 6 to 1 (lipid weight to oligomeric compound weight).

In certain embodiments, a composition of the invention comprises an oligomeric compound, a cationic lipid, a neutral lipid, a sterol, and a disaggregation lipid in a molar ratio of 57.5 to 7.5 to 31.5 to 3.5 wherein the cationic lipid is 2,2-Dilinoleyl-4-dimethylaminoethyl-[1,3]-dioxolane (XTC), the neutral lipid is distearoylphosphatidylcholine (DSPC), the sterol is cholesterol and the disaggregation lipid is PEG-didimyristoyl glycerol (PEG-DMG), and wherein the ratio of total lipid to oligomeric compound ratio is 11 to 1 (lipid weight to oligomeric compound weight).

In certain embodiments, a composition of the invention comprises an oligomeric compound, a cationic lipid, a neutral lipid, a sterol, and a disaggregation lipid in a molar ratio of 60 to 7.5 to 31 to 1.5 wherein the cationic lipid is 2,2-Dilinoleyl-4-dimethylaminoethyl-[1,3]-dioxolane (XTC), the neutral lipid is distearoylphosphatidylcholine (DSPC), the sterol is cholesterol and the disaggregation lipid is PEG-didimyristoyl glycerol (PEG-DMG), and wherein the ratio of total lipid to oligomeric compound ratio is 6 to 1 (lipid weight to oligomeric compound weight).

In certain embodiments, a composition of the invention comprises an oligomeric compound, a cationic lipid, a neutral lipid, a sterol, and a disaggregation lipid in a molar ratio of 60 to 7.5 to 31 to 1.5 wherein the cationic lipid is 2,2-Dilinoleyl-4-dimethylaminoethyl-[1,3]-dioxolane (XTC), the neutral lipid is distearoylphosphatidylcholine (DSPC), the sterol is cholesterol and the disaggregation lipid is PEG-didimyristoyl glycerol (PEG-DMG), and wherein the ratio of total lipid to oligomeric compound ratio is 11 to 1 (lipid weight to oligomeric compound weight).

In certain embodiments, a composition of the invention comprises an oligomeric compound, a cationic lipid, a neutral lipid, a sterol, and a disaggregation lipid in a molar ratio of 50 to 10 to 38.5 to 1.5 wherein the cationic lipid is 2,2-Dilinoleyl-4-dimethylaminoethyl-[1,3]-dioxolane (XTC), the neutral lipid is distearoylphosphatidylcholine (DSPC), the sterol is cholesterol and the disaggregation lipid is PEG-didimyristoyl glycerol (PEG-DMG), and wherein the ratio of total lipid to oligomeric compound ratio is 11 to 1 (lipid weight to oligomeric compound weight).

In certain embodiments, a composition of the invention comprises an oligomeric compound, a cationic lipid, a neutral lipid, a sterol, and a disaggregation lipid in a molar ratio of 50 to 10 to 38.5 to 1.5 wherein the cationic lipid is 2,2-Dilinoleyl-4-dimethylaminoethyl-[1,3]-dioxolane (XTC), the neutral lipid is distearoylphosphatidylcholine (DSPC), the sterol is cholesterol and the disaggregation lipid is PEG-didimyristoyl glycerol (PEG-DMG), and wherein the ratio of total lipid to oligomeric compound ratio is 10 to 1 (lipid weight to oligomeric compound weight).

In certain embodiments, a composition of the invention comprises a lipid, an aqueous component, and a non-ionic surfactant, wherein the lipid comprises 20-100% by weight of a neutral phospholipid and 0-80% by weight of an oil or wax; the aqueous component comprises an oligomeric compound in an aqueous medium; and the surfactant comprises 0.1-50% of the total emulsion by weight. In certain embodiments, the neutral phospholipid is 1,2-dioleoyi-sn-glycero-3-phosphocholine. In certain embodiments, the oil is squalene. In certain embodiments, the surfactant is polysorbate 20. In certain embodiments, the composition comprises an antioxidant. In certain embodiments, the lipid comprises 20-40% phospholipid and 60-80% oil or wax; and the surfactant comprises 40-50% of the total emulsion by weight. Additional lipid-containing compositions are described in US Patent Publication No. 20090306194, which is herein incorporated by reference in its entirety for the description of lipid-containing compositions.

Disaggregation Lipids

Examples of lipids that reduce aggregation of particles during formation include polyethylene glycol (PEG)-modified lipids, monosialoganglioside Gm1, and polyamide oligomers ("PAO") such as (described in U.S. Pat. No. 6,320, 017). Other compounds with uncharged, hydrophilic, steric-barrier moieties, which prevent aggregation during formulation, like PEG, Gm1 or ATTA, can also be coupled to lipids for use as in the methods and compositions of the invention. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 1 to 15% (by mole percent of lipids).

Specific examples of PEG-modified lipids (or lipid-polyoxyethylene conjugates) that are useful in the present invention can have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in co-pending U.S. Ser. No. 08/486,214, incorporated herein by reference, PEG-modified dialkylamines and PEG-modified 1,2-diacyloxypropan-3-amines. Particularly suitable are PEG-modified diacylglycerols and dialkylglycerols.

In embodiments where a sterically-large moiety such as PEG or ATTA are conjugated to a lipid anchor, the selection of the lipid anchor depends on what type of association the conjugate is to have with the lipid particle. It is well known that mPEG (mw2000)-diastearoylphosphatidylethanolamine (PEG-DSPE) will remain associated with a liposome until the particle is cleared from the circulation, possibly a matter of days. Other conjugates, such as PEG-CerC20 have similar staying capacity. PEG-CerC14, however, rapidly exchanges out of the formulation upon exposure to serum, with a $T_{1/2}$ less than 60 minutes in some assays. As illustrated in U.S. patent application Ser. No. 08/486,214, at least three characteristics influence the rate of exchange: length of acyl chain, saturation of acyl chain, and size of the steric-barrier head group. Compounds having suitable variations of these features may be useful for the invention. For some therapeutic applications it may be suitable for the PEG-modified lipid to be rapidly lost from the nucleic acid-lipid particle in vivo and hence the PEG-modified lipid will possess relatively short lipid anchors. In other therapeutic applications it may be suitable for the nucleic acid-lipid particle to exhibit a longer plasma circulation lifetime and hence the PEG-modified lipid will possess relatively longer lipid anchors.

It should be noted that aggregation preventing compounds do not necessarily require lipid conjugation to function properly. Free PEG or free ATTA in solution may be sufficient to prevent aggregation. If the particles are stable after formulation, the PEG or ATTA can be dialyzed away before administration to a subject.

Neutral Lipids

Neutral lipids, when present in the lipid particle, can be any of a number of lipid species which exist either in an uncharged or neutral zwitterionic form at physiological pH. Such lipids include, for example diacylphosphatidylcholine, diacylphosphatidylethanolamine, ceramide, sphingomyelin, dihydrosphingomyelin, cephalin, and cerebrosides. The selection of neutral lipids for use in the particles described herein is generally guided by consideration of, e.g., liposome size and stability of the liposomes in the bloodstream. Suitably, the neutral lipid component is a lipid having two acyl groups, (i.e., diacylphosphatidylcholine and diacylphosphatidylethanolamine). Lipids having a variety of acyl chain groups of varying chain length and degree of saturation are available or may be isolated or synthesized by well-known techniques. In one group of embodiments, lipids containing saturated fatty acids with carbon chain lengths in the range of $C_{10}$ to $C_{20}$ are suitable. In another group of embodiments, lipids with mono or diunsaturated fatty acids with carbon chain lengths in the range of $C_{10}$ to $C_{20}$ are used. Additionally, lipids having mixtures of saturated and unsaturated fatty acid chains can be used.

In certain embodiments, the neutral lipids used in the present invention include but are not limited to phosphatidylcholine (PC), 1,2-Dioleoyl-sn-glycero-3-phosphocholine (DOPC), lecithin, phosphatidylethanolamine (PE), lysolecithin, lysophosphatidylethanolamine, sphinogomyelin (SM), cardiolipin, phosphosphatidic acid, 1,2-Distearoyl-sn-glycero-3-phosphocholine (DSPC), 1,2-Dipalmitoyl-sn-glycero-3-phosphoethanolamine (DPPE), 1-Palmitoyl-2-oleoyl-sn-glycero-3-phosphocholine (POPC), 1,2-Dilauroyl-sn-glycero-3-phosphocholine (DLPC), 1,2-Dimyristoyi-sn-glycero-3-phosphocholine (DMPC), 1,2-Dipalmitoyl-sn-glycero-3-phosphocholine (DPPC), 1,2-Dimyristoyl-sn-glycero-3-phosphoethanolamine (DMPE), 1,2-Dioleoyl-sn-glycero-3-phosphoethanolamine (DOPE), dipalmitoloeoyl-PE, diphytanoyl-PE, DSPE, dielaidoyl-PE, dilinoleoyl-SM, and dilinoleoyl-PE. The neutral lipids useful in the present invention may also be composed of sphingomyelin, dihydrosphingomyeline, or phospholipids with other head groups, such as serine and inositol.

In certain embodiments, neutral lipids are DOPE, DSPC, POPC, DPPC or any related phosphatidylcholine.

Sterols

The sterol component of the lipid mixture, when present, can be any of those sterols conventionally used in the field of liposome, lipid vesicle or lipid particle preparation. In certain embodiments, the sterol is cholesterol.

Cationic Lipids

Cationic lipids, which carry a net positive charge at about physiological pH, may also be included in compositions of the present invention. Such cationic lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy) propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), and N-(1,2-dimyristyloxyprop-3-yl)-N,N-dimethyl-N-hydroxyethyl ammonium bromide ("DMRIE"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). In particular embodiments, a cationic lipid is an amino lipid.

Additional cationic lipids include 1,2-dilinoleyloxy-3-dimethylaminopropane (DLinDMA) 1,2-Dilinoleoyl-3-dimethylaminopropane (DLinDAP), 1-Linoleoyl-2-linoeyloxy-3-dimethylaminopropane (DLin-2-DMAP), 1,2-Dilinoleylcarbamoyloxy-3-dimethylaminopropane (DLin-C-DAP), 1,2-Dilinoleylthio-3-dimethylaminopropane (DLin-S-DMA), 2,2-Dilinoleyl-4-dimethylaminomethyl-[1,3]-dioxolane (DLin-K-DMA).

Anionic lipids suitable for use in lipid particles of the present invention include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

In certain embodiments, compositions of the invention include amphipathic lipids. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and α-acyloxyacids, can also be used. Additionally, such amphipathic lipids can be readily mixed with other lipids, such as triglycerides and sterols.

Also suitable for inclusion in compositions of the present invention are programmable fusion lipids. Such lipid particles have little tendency to fuse with cell membranes and deliver their payload until a given signal event occurs. This allows the lipid particle to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the lipid particle membrane over time. By the time the lipid particle is suitably distributed in the body, it has lost sufficient cloaking agent so as to be fusogenic. With other signal events, it is desirable to choose a signal that is associated with the disease site or target cell, such as increased temperature at a site of inflammation.

In certain embodiments, it is desirable to target compositions of the invention using targeting moieties that are specific to a cell type or tissue. Targeting of lipid particles using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044). The targeting moieties can comprise the entire protein or fragments thereof. Targeting mechanisms generally require that the targeting agents be positioned on the surface of the lipid particle in such a manner that the target moiety is available for interaction with the target, for example, a cell surface receptor. A variety of different targeting agents and methods are known and available in the art, including those described, e.g., in Sapra, P. and Allen, T M, *Frog. Lipid Res.* 42(5):439-62 (2003); and Abra, R M et al., *J. Liposome Res.* 12:1-3, (2002).

The use of lipid particles, i.e., liposomes, with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013, 556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). In one approach, a ligand, such as an antibody, for targeting the lipid particle is linked to the polar head group of lipids forming the lipid particle. In another approach, the targeting ligand is attached to the distal ends of the PEG chains forming the hydrophilic polymer coating (Klibanov, et al., *Journal of Liposome Research* 2: 321-334 (1992); Kirpotin et al., *FEBS Letters* 388: 115-118 (1996)).

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337-16342 (1990) and Leonetti, et al., *Proc. Natl. Acad. Sci.* (*USA*), 87:2448-2451 (1990). Other examples of antibody conjugation are disclosed in U.S. Pat. No. 6,027,726, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes,* 149 *Methods in Enzymology* 111-119 (Academic Press, Inc. 1987)). Other targeting methods include the biotin-avidin system.

Certain Oligomeric Compounds

Provided herein are oligomeric compounds that are designed to mimic miR-34 activity. In certain embodiments, the oligomeric compounds comprising oligonucleotides having nucleobase identity to the nucleobase sequence of miR-34a, and are thus designed to mimic miR-34a activity. In certain embodiments, the oligomeric compounds comprising oligonucleotides having nucleobase identity to the nucleobase sequence of miR-34b, and are thus designed to mimic miR-34a activity. In certain embodiments, the oligomeric compounds comprising oligonucleotides having nucleobase identity to the nucleobase sequence of miR-34c, and are thus designed to mimic miR-34a activity. In certain embodiments, the oligomeric compound comprises an oligonucleotide. In certain embodiments, the oligomeric compound comprises an oligonucleotide hybridized to a complementary strand.

Compositions of the present invention comprise oligomeric compounds comprising oligonucleotides having nucleobase sequences that share identity with endogenous miRNA or miRNA precursor nucleobase sequences. An oligonucleotide selected for inclusion in a composition of the present invention may be one of a number of lengths. Such an oligonucleotide can be from 7 to 100 linked nucleosides in length. For example, an oligonucleotide sharing nucleobase identity with a miRNA may be from 7 to 30 linked nucleosides in length. An oligonucleotide sharing identity with a miRNA precursor may be up to 100 linked nucleosides in length.

In certain embodiments, an oligonucleotide consists of 7 to 30 linked nucleosides. In certain embodiments, an oligonucleotide consists of 7, 8, 9, 10, 11, 12, 13, 14, 15, 16, 17, 18, 19, 20, 21, 22, 23, 24, 25, 26, 28, 29, or 30 linked nucleotides.

In certain embodiments, an oligonucleotide consists of 15 to 30 linked nucleosides. In certain embodiments, an oligonucleotide consists of 15 linked nucleosides. In certain embodiments, an oligonucleotide consists of 16 linked nucleosides. In certain embodiments, an oligonucleotide consists of 17 linked nucleosides. In certain embodiments, an oligonucleotide consists of 18 linked nucleosides. In certain embodiments, an oligonucleotide consists of 19 linked nucleosides. In certain embodiments, an oligonucleotide consists of 20 linked nucleosides. In certain embodiments, an oligonucleotide consists of 21 linked nucleosides. In certain embodiments, an oligonucleotide consists of 22 linked nucleosides. In certain embodiments, an oligonucleotide consists of 23 linked nucleosides. In certain embodiments, an oligonucleotide consists of 24 linked nucleosides. In certain embodiments, an oligonucleotide consists of 25 linked nucleosides. In certain embodiments, an oligonucleotide consists of 26 linked nucleosides. In certain embodiments, an oligonucleotide consists of 27 linked nucleosides. In certain embodiments, an oligonucleotide consists of 28 linked nucleosides. In certain embodiments, an oligonucleotide consists of 29 linked nucleosides. In certain embodiments, an oligonucleotide consists of 30 linked nucleosides.

In certain embodiments, an oligonucleotide consists of 19 to 23 linked nucleosides. In certain embodiments, an oligonucleotide is from 40 up to 50, 60, 70, 80, 90, or 100 linked nucleosides in length.

In certain embodiments, an oligonucleotide has a sequence that has a certain identity to a miRNA or a precursor thereof. Nucleobase sequences of mature miRNAs and their corresponding stem-loop sequences described herein are the sequences found in miRBase, an online searchable database of miRNA sequences and annotation, found at the website microRNA"dot"sanger"dot"ac"dot"uk. Entries in the miRBase Sequence database represent a predicted hairpin portion of a miRNA transcript (the stem-loop), with information on the location and sequence of the mature miRNA sequence. The miRNA stem-loop sequences in the database are not strictly precursor miRNAs (pre-miRNAs), and may in some instances include the pre-miRNA and some flanking sequence from the presumed primary transcript. The miRNA nucleobase sequences described herein encompass any version of the miRNA, including the sequences described in Release 10.0 of the miRBase sequence database and sequences described in any earlier Release of the miRBase sequence database. A sequence database release may result in the re-naming of certain miRNAs. A sequence database release may result in a variation of a mature miRNA sequence. The compositions of the present invention encompass oligomeric compound comprising oligonucleotides having a certain identity to any nucleobase sequence version of a miRNAs described herein.

In certain embodiments, an oligonucleotide has a nucleobase sequence at least 60%, 65%, 70%, 75%, 80%, 85%, 90%, 95%, 97%, 98% or 99% identical to the miRNA over a region of 7, 8, 9, 10, 11, 12, 13, 14, 15, 16, 17, 18, 19, 20, 21, 22, 23, 24, 25, 26, 27, 28, 29, or 30 nucleobases. Accordingly, in certain embodiments the nucleobase sequence of an oligonucleotide may have one or more non-identical nucleobases with respect to the miRNA. In certain embodiments, the miRNA is miR-34. In certain embodiments, the miR-34 is miR-34a. In certain embodiments, the miR-34 is miR-34b. In certain embodiments, the miR-34 is miR-34c. In certain embodiments, the miR-34a has the nucleobase sequence of SEQ ID NO: 1. In certain embodiments, the miR-34c has the nucleobase sequence of SEQ ID NO: 2.

In certain embodiments, an oligonucleotide has a nucleobase sequence at least 60%, 65%, 70%, 75%, 80%, 85%, 90%, 95%, 97%, 98% or 99% identical to the precursor over a region of 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleobases. In certain embodiments, the miRNA precursor is a miR-34 precursor. In certain embodiments the miR-34 precursor is a miR-34a precursor. In certain embodiments, the miR-34a precursor is a miRNA stem-loop sequence selected from the miR-34a stem-loop sequence (SEQ ID NO: 4; GGCCAGCUGUGAGUGUUU CUUUGGCAGUGUCUUAGCUGGUUGUU-GUGAGCAAUAGUAAGGAAGCAAUCAGCA AGUAUACUGCCCUAGAAGUGCUGCACG-UUGUGGGCCC). In certain embodiments, the miR-34 precursor is the miR-34b stem-loop sequence (SEQ ID NO: 5; GUGCUCGGUUUGUA GGCAGUGUCA-UUAGCUGAUUGUACUGUGGUGGUUA-CAAUCACUAACUCCACUGC CAUCAAAACAAG-GCAC). In certain embodiments, the miR-34 precursor is the miR-34c stem-loop sequence (SEQ ID NO: 6; AGUCUAG-UUACUAGGCAGUGUAGUUAGCUGAU UGC-UAAUAGUACCAAUCACUAACCACACGGC-CAGGUAAAAAGAUU).

In certain embodiments, an oligonucleotide consists of a number of linked nucleosides that is equal to the length of the miRNA or precursor thereof with which it shares identity.

In certain embodiments, the number of linked nucleosides of an oligonucleotide is less than the length of the miRNA or precursor thereof with which it shares identity. In certain such embodiments, the number of linked nucleosides of an oligonucleotide is one less than the length of the miRNA or precursor thereof with which it shares identity. In certain such embodiments, an oligonucleotide has one less nucleoside at the 5' terminus. In certain such embodiments, an oligonucleotide has one less nucleoside at the 3' terminus. In certain such embodiments, an oligonucleotide has two fewer nucleosides at the 5' terminus. In certain such embodiments, an oligonucleotide has two fewer nucleosides at the 3' terminus. An oligonucleotide having a number of linked nucleosides that is less than the length of the miRNA or precursor thereof, wherein each nucleobase of an oligonucleotide is identical to each nucleobase at a corresponding position in a miRNA or precursor thereof, is considered to be an oligonucleotide having a nucleobase sequence that is 100% identical to a region of the miRNA or precursor thereof.

In certain embodiments, the number of linked nucleosides of an oligonucleotide is greater than the length of the miRNA or precursor thereof with which it shares identity. In certain embodiments, the number of linked nucleosides of an oligonucleotide is one greater than the length of the miRNA or precursor thereof with which it shares identity. In certain such embodiments, the additional nucleoside is at the 5' terminus of an oligonucleotide. In certain such embodiments, the additional nucleoside is at the 3' terminus of an oligonucleotide. In certain embodiments, the number of linked nucleosides of an oligonucleotide is two greater than the length of the miRNA or precursor thereof with which it shares identity. In certain such embodiments, the two additional nucleosides are at the 5' terminus of an oligonucleotide. In certain such embodiments, the two additional nucleosides are at the 3' terminus of an oligonucleotide. In certain such embodiments, one additional nucleoside is located at the 5' terminus and one additional nucleoside is located at the 3' terminus of an oligonucleotide. In certain such embodiments, the nucleobase of an additional nucleoside may or may not be identical to the corresponding nucleobase of the endogenous miRNA or precursor thereof.

Compositions of the present invention may comprise oligonucleotides having a percentage region identity and percentage overall identity that are different from one another. In certain embodiments, a region of the nucleobase sequence of an oligonucleotide is 100% identical to the nucleobase sequence of the miRNA, but the oligonucleotide does not have 100% overall identity to the entire miRNA. In certain such embodiments, the number of nucleosides of the oligonucleotide is greater than the length of the miRNA, but the oligonucleotide has a region that is 100% identical to the miRNA. For example, an oligonucleotide consisting of 24 linked nucleosides, where the nucleobases of nucleosides 1 through 23 are each identical to a corresponding position of a miRNA that is 23 nucleobases in length, has a 23 nucleoside region that is fully identical to the nucleobase sequence of the miRNA and approximately 96% overall identity to the nucleobase sequence of the miRNA. For example, an oligonucleotide consisting of 22 linked nucleosides, where the nucleobases of nucleosides 1 through 22 are each identical to a corresponding position of a miRNA that is 23 nucleobases in length, is fully complementary to a 22 nucleobase region of the nucleobase sequence of a miRNA. Such an oligonucleotide has approximately 96% overall identity to the nucleobase sequence of the entire miRNA, and has 100% identity to a 22 nucleobase region of the miRNA.

In certain embodiments, a region of the nucleobase sequence of an oligonucleotide is 100% identical to a region of the nucleobase sequence of a miRNA, or a precursor thereof. In certain such embodiments, 15 contiguous nucleobases of an oligonucleotide are each identical to 15 contiguous nucleobases of a miRNA, or a precursor thereof. In certain such embodiments, 16 contiguous nucleobases of an oligonucleotide are each identical to 16 contiguous nucleobases of a miRNA, or a precursor thereof. In certain such embodiments, 17 contiguous nucleobases of an oligonucleotide are each identical to 17 contiguous nucleobases of a miRNA, or a precursor thereof. In certain such embodiments, 18 contiguous nucleobases of an oligonucleotide are each identical to 18 contiguous nucleobases of a miRNA, or a precursor thereof. In certain such embodiments, 19 contiguous nucleobases of an oligonucleotide are each identical to 19 contiguous nucleobases of a miRNA, or a precursor thereof. In certain such embodiments, 20 contiguous nucleobases of an oligonucleotide are each identical to 20 contiguous nucleobases of a miRNA, or a precursor thereof. In certain such embodiments, 22 contiguous nucleobases of an oligonucleotide are each identical to 22 contiguous nucleobases of a miRNA, or a precursor thereof. In certain such embodiments, 23 contiguous nucleobases of an oligonucleotide are each identical to 23 contiguous nucleobases of a miRNA, or a precursor thereof. In certain such embodiments, 24 contiguous nucleobases of an oligonucleotide are each identical to 24 contiguous nucleobases of a miRNA, or a precursor thereof. In certain of these embodiments, the contiguous nucleobases comprise nucleobases 1-7, 2-7, 1-8, or 2-8 of a miRNA seed sequence.

Compositions of the present invention may comprise oligonucleotides having seed region identity with a miRNA. In certain embodiments, the nucleobase sequence of an oligonucleotide has at least 80% seed region identity with the nucleobase sequence of a miRNA. In certain embodiments, the nucleobase sequence of an oligonucleotide has at least 85% seed region identity with the nucleobase sequence of a miRNA. In certain embodiments, the nucleobase sequence of an oligonucleotide has at least 90% seed region identity with the nucleobase sequence of a miRNA. In certain embodiments, the nucleobase sequence of an oligonucleotide has at least 95% seed region identity with the nucleobase sequence of a miRNA. In certain embodiments, the nucleobase sequence of an oligonucleotide has 100% seed region identity with the nucleobase sequence of a miRNA.

The seed region of a miRNA may comprise one of several sequences, thus seed region identity may be calculated differently depending on the selection of a particular seed sequence. In certain embodiments, the seed region of a miRNA comprises nucleobases 2-7 of the miRNA. In certain embodiments, the seed region of a miRNA comprises nucleobases 1-7 of the miRNA. In certain embodiments, the seed region of a miRNA comprises nucleobases 2-8 of the miRNA. In certain embodiments, the seed region of a miRNA comprises nucleobases 1-8 of the miRNA.

In certain embodiments, the nucleobase sequence of an oligonucleotide has at least 80% seed region identity with the nucleobase sequence of a miRNA, and at least 80% overall identity with the miRNA. In certain embodiments, the nucleobase sequence of an oligonucleotide has at least 80% seed region identity with the nucleobase sequence of a miRNA, and at least 85% overall identity with the miRNA. In certain embodiments, the nucleobase sequence of an oligonucleotide has at least 80% seed region identity with the nucleobase sequence of a miRNA, and at least 90% overall identity with the miRNA. In certain embodiments, the nucleobase sequence of an oligonucleotide has at least 80% seed region identity with the nucleobase sequence of a miRNA, and at least 95% overall identity with the miRNA. In certain embodiments, the nucleobase sequence of an oligonucleotide has at least 80% seed region identity with the nucleobase sequence of a miRNA, and 100% overall identity with the miRNA.

In certain embodiments, the nucleobase sequence of an oligonucleotide has at least 85% seed region identity with the nucleobase sequence of a miRNA, and at least 80% overall identity with the miRNA. In certain embodiments, the nucleobase sequence of an oligonucleotide has at least 85% seed region identity with the nucleobase sequence of a miRNA, and at least 85% overall identity with the miRNA. In certain embodiments, the nucleobase sequence of an oligonucleotide has at least 85% seed region identity with the nucleobase sequence of a miRNA, and at least 90% overall identity with the miRNA. In certain embodiments, the nucleobase sequence of an oligonucleotide has at least 85% seed region identity with the nucleobase sequence of a miRNA, and at least 95% overall identity with the miRNA. In certain embodiments, the nucleobase sequence of an oligonucleotide has at least 85% seed region identity with the nucleobase sequence of a miRNA, and 100% overall identity with the miRNA.

In certain embodiments, the nucleobase sequence of an oligonucleotide has at least 90% seed region identity with the nucleobase sequence of a miRNA, and at least 80% overall identity with the miRNA. In certain embodiments, the nucleobase sequence of an oligonucleotide has at least 90% seed region identity with the nucleobase sequence of a miRNA, and at least 85% overall identity with the miRNA. In certain embodiments, the nucleobase sequence of an oligonucleotide has at least 90% seed region identity with the nucleobase sequence of a miRNA, and at least 90% overall identity with the miRNA. In certain embodiments, the nucleobase sequence of an oligonucleotide has at least 90% seed region identity with the nucleobase sequence of a miRNA, and at least 95% overall identity with the miRNA. In certain embodiments, the nucleobase sequence of an oligonucleotide has at least 90% seed region identity with the nucleobase sequence of a miRNA, and 100% overall identity with the miRNA.

In certain embodiments, the nucleobase sequence of an oligonucleotide has at least 95% seed region identity with the nucleobase sequence of a miRNA, and at least 80% overall identity with the miRNA. In certain embodiments, the nucleobase sequence of an oligonucleotide has at least 95% seed region identity with the nucleobase sequence of a miRNA, and at least 85% overall identity with the miRNA. In certain embodiments, the nucleobase sequence of an oligonucleotide has at least 95% seed region identity with the nucleobase sequence of a miRNA, and at least 90% overall identity with the miRNA. In certain embodiments, the nucleobase sequence of an oligonucleotide has at least 95% seed region identity with the nucleobase sequence of a miRNA, and at least 95% overall identity with the miRNA. In certain embodiments, the nucleobase sequence of an oligonucleotide has at least 95% seed region identity with the nucleobase sequence of a miRNA, and 100% overall identity with the miRNA.

In certain embodiments, the nucleobase sequence of an oligonucleotide has 100% seed region identity with the nucleobase sequence of a miRNA, and at least 80% overall identity with the miRNA. In certain embodiments, the nucleobase sequence of an oligonucleotide has 100% seed region identity with the nucleobase sequence of a miRNA, and at least 85% overall identity with the miRNA. In certain embodiments, the nucleobase sequence of an oligonucleotide has 100% seed region identity with the nucleobase sequence of a miRNA, and at least 90% overall identity with the miRNA. In certain embodiments, the nucleobase sequence of an oligonucleotide has 100% seed region identity with the nucleobase sequence of a miRNA, and at least 95% overall identity with the miRNA. In certain embodiments, the nucleobase sequence of an oligonucleotide has 100% seed region identity with the nucleobase sequence of a miRNA, and 100% overall identity with the miRNA.

In certain embodiments, an oligonucleotide has a nucleobase sequence having one non-identical nucleobase with respect to the nucleobase sequence of a mature miRNA, or a precursor thereof. In certain embodiments, an oligonucleotide has a nucleobase sequence having two non-identical nucleobases with respect to the nucleobase sequence of a miRNA, or a precursor thereof. In certain such embodiments, an oligonucleotide has a nucleobase sequence having no more than two non-identical nucleobases with respect to the nucleobase sequence of a mature miRNA, or a precursor thereof. In certain such embodiments, the non-identical nucleobases are contiguous. In certain such embodiments, the non-identical nucleobases are not contiguous.

In certain embodiments, an oligomeric compound for use in a composition described herein comprises an oligonucleotide hybridized to a complementary oligonucleotide, i.e. the oligomeric compound is a double-stranded oligomeric compound.

A double-stranded oligomeric compound may be from 7 to 30 basepairs in length. In certain embodiments, a double-stranded oligomeric compound is from 15 to 30 basepairs in length. In certain embodiments, a double-stranded oligomeric compound is from 19 to 23 basepairs in length. In certain embodiments, a double-stranded oligomeric compound is 19 basepairs in length. In certain embodiments, a double-stranded oligomeric compound is 20 basepairs in length. In certain embodiments, a double-stranded oligomeric compound is 21 basepairs in length. In certain embodiments, a double-stranded oligomeric compound is 22 basepairs in length. In certain embodiments, a double-stranded oligomeric compound is 23 basepairs in length.

In certain embodiments, the hybridization of an oligonucleotide to a complementary oligonucleotide forms at least one blunt end. In certain such embodiments, the hybridization of an oligonucleotide to a complementary oligonucleotide forms a blunt end at each terminus of the double-stranded oligomeric compound.

The hybridization of an oligonucleotide to a complementary oligonucleotide may result in the formation of one or more overhangs, where one or more additional nucleosides of at least one terminus of the oligonucleotide do not have a corresponding nucleobase in the complementary oligonucleotide with which to pair through hydrogen bonding. In such cases, the hybridization of the oligonucleotide to the complementary oligonucleotide results in the formation of a central complementary region. The central complementary region can tolerate mismatches, provided that there is sufficient complementarity to permit hybridization. In certain embodiments, there are 0, 1, 2, or 3 mismatches in the central complementary region.

In certain embodiments, a terminus of an oligonucleotide comprises one or more additional linked nucleosides relative to the number of linked nucleosides of the complementary oligonucleotide. In certain embodiments, the one or more additional nucleosides are at the 5' terminus of an oligonucleotide. In certain embodiments, the one or more additional nucleosides are at the 3' terminus of an oligonucleotide. In certain embodiments, at least one nucleobase of a nucleoside of the one or more additional nucleosides is complementary to the target RNA. In certain embodiments, each nucleobase of each one or more additional nucleosides is complementary to the target RNA. In certain embodiments, a terminus of the complementary oligonucleotide comprises one or more additional linked nucleosides relative to the number of linked nucleosides of an oligonucleotide. In certain embodiments, the one or more additional linked nucleosides are at the 3' terminus of the complementary oligonucleotide. In certain embodiments, the one or more additional linked nucleosides are at the 5' terminus of the complementary oligonucleotide. In certain embodiments, two additional linked nucleosides are linked to a terminus. In certain embodiments, one additional nucleoside is linked to a terminus.

In certain embodiments, a composition of the present invention comprises an oligomeric compound comprising an oligonucleotide having nucleobase identity to miR-34 and a complementary oligonucleotide.

In certain embodiments, the oligonucleotide has the nucleobase sequence of SEQ ID NO: 1 (UGGCAGUGUCU- UAGCUGGUUGU) and the complementary oligonucleotide has the sequence of SEQ ID NO: 7 (AACCAGCUAAGA-CACUGCCAAA). The oligonucleotide and complementary oligonucleotide are annealed to form the following double-stranded oligomeric compound structure, where the oligonucleotide and complementary oligonucleotide comprise 20 base pairs, and each of the oligonucleotide and complementary oligonucleotide has an additional 2 nucleosides at the 3' terminus that form overhangs (the central complementary portion is underscored):

```
                                              (SEQ ID NO: 1)
        UGGCAGUGUCUUAGCUGGUUGU (SEQ ID NO: 7)
        AAACCGUCACAGAAUCGACCAA
```

In certain embodiments the oligonucleotide has the nucleobase sequence of SEQ ID NO: 1 and the complementary oligonucleotide is 22 linked nucleosides in length and comprises nucleobases 1 to 20 of SEQ ID NO: 7, where the two nucleosides at the 3' terminus of the complementary oligonucleotide are independently selected from A, C, T and G.

In certain embodiments, the complementary oligonucleotide is less than 100% complementary to the oligonucleotide. In certain embodiments, the complementary oligonucleotide has at least one mismatch relative to the oligonucleotide. In certain embodiments, the complementary oligonucleotide has two mismatches relative to the oligonucleotide. In certain embodiments, at least one mismatch is located between the second nucleobase of the oligonucleotide and the corresponding nucleobase of the complementary oligonucleotide.

In certain embodiments, the oligomeric compound comprises an oligonucleotide conjugated to one or more moieties which enhance the activity, cellular distribution or cellular uptake of the resulting antisense oligonucleotides. In certain such embodiments, the moiety is a cholesterol moiety or a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, a conjugate group is attached directly to an oligonucleotide. In certain embodiments, a conjugate group is attached to an oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted $C_1$-$C_{10}$ alkyl, substituted or unsubstituted $C_2$-$C_{10}$ alkenyl, and substituted or unsubstituted $C_2$-$C_{10}$ alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the oligomeric compound comprises an oligonucleotide having one or more stabilizing groups that are attached to one or both termini of the oligonucleotide to enhance properties such as, for example, nuclease stability. Included in stabilizing groups are cap structures. These terminal modifications protect an oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Suitable cap structures include a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-aminoalkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

The nucleobase sequences set forth herein, including but not limited to those found in the Examples and in the sequence listing, are independent of any modification to the nucleic acid. As such, nucleic acids defined by a SEQ ID NO may comprise, independently, one or more modifications to one or more sugar moieties, to one or more internucleoside linkages, and/or to one or more nucleobases.

Although the sequence listing accompanying this filing identifies each nucleobase sequence as either "RNA" or "DNA" as required, in reality, those sequences may be modified with any combination of chemical modifications. One of skill in the art will readily appreciate that such designation as "RNA" or "DNA" to describe modified oligonucleotides is somewhat arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine(methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$C-GAUCG," wherein $^{me}$C indicates a cytosine base comprising a methyl group at the 5-position.

Oligomeric compounds described herein by Regulus Number (RG#) comprise a combination of nucleobase sequence and may comprise certain identified modifications.

Certain Modifications

Oligonucleotides of the present invention comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, an oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In certain embodiments, the bicyclic sugar moiety comprises a bridge group between the T and the 4'-carbon atoms. In certain such embodiments, the bridge group comprises from 1 to 8 linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N($R_1$)—, —C($R_1$)($R_2$)—, —C($R_1$)=C($R_1$)—, —C($R_1$)=N—, —C(=N$R_1$)—, —Si($R_1$)($R_2$)—, —S(=O)$_2$—, —S(=O)—, —C(=O)— and —C(=S)—; where each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, amino, substituted amino, acyl, substituted acyl, $C_1$-$C_{12}$ aminoalkyl, $C_1$-$C_{12}$ aminoalkoxy, substituted $C_1$-$C_{12}$ aminoalkyl, substituted $C_1$-$C_{12}$ aminoalkoxy or a protecting group.

In some embodiments, the bicyclic sugar moiety is bridged between the 2' and 4' carbon atoms with a biradical group selected from —O—(CH$_2$)$_p$—, —O—CH$_2$—, —O—CH$_2$CH$_2$—, —O—CH(alkyl)-, —NH—(CH$_2$)$_p$—, —N(alkyl)-(CH$_2$)$_p$—, —O—CH(alkyl)-, —(CH(alkyl))-(CH$_2$)$_p$—, —NH—O—(CH$_2$)$_p$—, —N(alkyl)-O—(CH$_2$)$_p$—, or —O—N(alkyl)-(CH$_2$)$_p$—, wherein p is 1, 2, 3, 4 or 5 and each alkyl group can be further substituted. In certain embodiments, p is 1, 2 or 3.

In certain embodiments, a 2'-modified nucleoside comprises a T-substituent group selected from halo, allyl, amino, azido, SH, CN, OCN, CF$_3$, OCF$_3$, O—, S—, or N($R_m$)-alkyl; O—, S—, or N($R_m$)-alkenyl; O—, S— or N($R_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N($R_m$)($R_n$) or O—CH$_2$—C(=O)—N($R_m$)($R_n$), where each $R_m$ and $R_n$ is, independently, H, an amino protecting group or substituted or unsubstituted $C_1$-$C_{10}$ alkyl. These T-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-modified nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N($R_m$)($R_n$), —O(CH$_2$)$_2$O(CH$_2$)$_2$N(CH$_3$)$_2$, and N-substituted acetamide (O—CH$_2$—C(=O)—N($R_m$)($R_n$) where each $R_m$ and $R_n$ is, independently, H, an amino protecting group or substituted or unsubstituted $C_1$-$C_{10}$ alkyl.

In certain embodiments, a 2'-modified nucleoside comprises a 2'-substituent group selected from F, OCF$_3$, O—CH$_3$, OCH$_2$CH$_2$OCH$_3$, 2'-O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-modified nucleoside comprises a 2'-substituent group selected from F, O—CH$_3$, and OCH$_2$CH$_2$OCH$_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4'-O replaced with 4'-S. A 4'-thio-2'-modified nucleoside is a 4'-thio modified nucleoside having the 2'-OH replaced with a 2'-substituent group. Suitable 2'-substituent groups include T-OCH$_3$, 2'-O—(CH$_2$)$_2$—OCH$_3$, and 2'-F.

In certain embodiments, an oligonucleotide of the present invention comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, an oligonucleotide of the present invention comprises at least one phosphorothioate internucleoside linkage. In certain embodiments, each internucleoside linkage of a modified oligonucleotide is a phosphorothioate internucleoside linkage.

In certain embodiments, a modified internucleoside linkage does not comprise a phosphorus atom. In certain such embodiments, an internucleoside linkage is formed by a short chain alkyl internucleoside linkage. In certain such embodiments, an internucleoside linkage is formed by a cycloalkyl internucleoside linkages. In certain such embodiments, an internucleoside linkage is formed by a mixed heteroatom and alkyl internucleoside linkage. In certain such embodiments, an internucleoside linkage is formed by a mixed heteroatom and cycloalkyl internucleoside linkages. In certain such embodiments, an internucleoside linkage is formed by one or more short chain heteroatomic internucleoside linkages. In certain such embodiments, an internucleoside linkage is formed by one or more heterocyclic internucleoside linkages. In certain such embodiments, an internucleoside linkage has an amide backbone. In certain such embodiments, an internucleoside linkage has mixed N, O, S and CH$_2$ component parts.

In certain embodiments, an oligonucleotide comprises one or more modified nucleobases. In certain embodiments, a modified oligonucleotide comprises one or more 5-methylcytosines. In certain embodiments, each cytosine of a modified oligonucleotide comprises a 5-methylcytosine.

In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

Certain Oligonucleotide Motifs

Suitable motifs for modified oligonucleotides of the present invention include, but are not limited to, fully modified, uniformly modified, positionally modified, and gapmer. Modified oligonucleotides having a fully modified motif, including a uniformly modified motif, may be designed to target mature miRNAs. Alternatively, modified oligonucleotides having a fully modified motif, including a uniformly modified motif, may be designed to target certain sites of pri-miRNAs or pre-miRNAs, to block the processing of miRNA precursors into mature miRNAs. Modified oligonucleotides having a fully modified motif or uniformly modified motif are effective inhibitors of miRNA activity.

In certain embodiments, a fully modified oligonucleotide comprises a sugar modification at each nucleoside. In certain such embodiments, pluralities of nucleosides are 2'-O-methoxyethyl nucleosides and the remaining nucleosides are 2'-fluoro nucleosides. In certain such embodiments, each of a plurality of nucleosides is a 2'-O-methoxyethyl nucleoside and each of a plurality of nucleosides is a bicyclic nucleoside. In certain such embodiments, a fully modified oligonucleotide further comprises at least one modified internucleoside linkage. In certain such embodiments, each internucleoside linkage of a fully sugar-modified oligonucleotide is a modified internucleoside linkage. In certain embodiments, a fully sugar-modified oligonucleotide further comprises at least one phosphorothioate internucleoside linkage. In certain such embodiments, each internucleoside linkage of a fully sugar-modified oligonucleotide is a phosphorothioate internucleoside linkage.

In certain embodiments, a fully modified oligonucleotide is modified at each internucleoside linkage. In certain such embodiments, each internucleoside linkage of a fully modified oligonucleotide is a phosphorothioate internucleoside linkage.

In certain embodiments, a uniformly modified oligonucleotide comprises the same sugar modification at each nucleoside. In certain such embodiments, each nucleoside of a modified oligonucleotide comprises a 2'-O-methoxyethyl sugar modification. In certain embodiments, each nucleoside of a modified oligonucleotide comprises a 2'-O-methyl sugar modification. In certain embodiments, each nucleoside of a modified oligonucleotide comprises a 2'-fluoro sugar modification. In certain such embodiments, a uniformly modified oligonucleotide further comprises at least one modified internucleoside linkage. In certain such embodiments, each internucleoside linkage of a uniformly sugar-modified oligonucleotide is a modified internucleoside linkage. In certain embodiments, a uniformly sugar-modified oligonucleotide further comprises at least one phosphorothioate internucleoside linkage. In certain such embodiments, each internucleoside linkage of a uniformly sugar-modified oligonucleotide is a phosphorothioate internucleoside linkage.

In certain embodiments, a uniformly modified oligonucleoside comprises the same internucleoside linkage modifications throughout. In certain such embodiments, each internucleoside linkage of a uniformly modified oligonucleotide is a phosphorothioate internucleoside linkage.

In certain embodiments, a positionally modified oligonucleotide comprises regions of linked nucleosides, where each nucleoside of each region comprises the same sugar moiety, and where each nucleoside of each region comprises a sugar moiety different from that of an adjacent region.

A modified oligonucleotide having a gapmer motif may have an internal region consisting of linked 2'-deoxynucleotides, and external regions consisting of linked 2'-modified nucleosides. Such a gapmer may be designed to elicit RNase H cleavage of a miRNA precursor. The internal 2'-deoxynucleoside region serves as a substrate for RNase H, allowing the cleavage of the miRNA precursor to which a modified oligonucleotide is targeted. In certain embodiments, each nucleoside of each external region comprises the same 2'-modified nucleoside. In certain embodiments, one external region is uniformly comprised of a first 2'-modified nucleoside and the other external region is uniformly comprised of a second 2'-modified nucleoside.

A modified oligonucleotide having a gapmer motif may have a sugar modification at each nucleoside. In certain embodiments, the internal region is uniformly comprised of a first 2'-modified nucleoside and each of the wings is uniformly comprised of a second 2'-modified nucleoside. In certain such embodiments, the internal region is uniformly comprised of 2'-fluoro nucleosides and each external region is uniformly comprised of 2'-O-methoxyethyl nucleosides.

In certain embodiments, each external region of a gapmer consists of linked 2'-O-methoxyethyl nucleosides. In certain embodiments, each external region of a gapmer consists of linked 2'-O-methyl nucleosides. In certain embodiments, each external region of a gapmer consists of 2'-fluoro nucleosides. In certain embodiments, each external region of a gapmer consists of linked bicyclic nucleosides.

In certain embodiments, each nucleoside of one external region of a gapmer comprises 2'-O-methoxyethyl nucleosides and each nucleoside of the other external region comprises a different 2'-modification. In certain such embodiments, each nucleoside of one external region of a gapmer comprises 2'-O-methoxyethyl nucleosides and each nucleoside of the other external region comprises 2'-O-methyl nucleosides. In certain such embodiments, each nucleoside of one external region of a gapmer comprises 2'-O-methoxyethyl nucleosides and each nucleoside of the other external region comprises 2'-fluoro nucleosides. In certain such embodiments, each nucleoside of one external region of a gapmer comprises 2'-O-methyl nucleosides and each nucleoside of the other external region comprises 2'-fluoro nucleosides. In certain such embodiments, each nucleoside of one external region of a gapmer comprises 2'-O-methoxyethyl nucleosides and each nucleoside of the other external region comprises bicyclic nucleosides. In certain such embodiments, each nucleoside of one external region of a gapmer comprises 2'-O-methyl nucleosides and each nucleoside of the other external region comprises bicyclic nucleosides.

In certain embodiments, nucleosides of one external region comprise two or more sugar modifications. In certain embodiments, nucleosides of each external region comprise two or more sugar modifications. In certain embodiments, at least one nucleoside of an external region comprises a 2'-O-methoxyethyl sugar and at least one nucleoside of the same external region comprises a 2'-fluoro sugar. In certain embodiments, at least one nucleoside of an external region comprises a 2'-O-methoxyethyl sugar and at least one nucleoside of the same external region comprises a bicyclic sugar moiety. In certain embodiments, at least one nucleoside of an external region comprises a 2'-O-methyl sugar and at least one nucleoside of the same external region comprises a bicyclic sugar moiety. In certain embodiments at least one nucleoside of an external region comprises a 2'-O-methyl sugar and at least one nucleoside of the same external region comprises a 2'-fluoro sugar. In certain embodiments, at least one nucleoside of an external region comprises a 2'-fluoro sugar and at least one nucleoside of the same external region comprises a bicyclic sugar moiety.

In certain embodiments, each external region of a gapmer consists of the same number of linked nucleosides. In certain embodiments, one external region of a gapmer consists a number of linked nucleosides different that that of the other external region.

In certain embodiments, the external regions comprise, independently, from 1 to 6 nucleosides. In certain embodiments, an external region comprises 1 nucleoside. In certain embodiments, an external region comprises 2 nucleosides. In certain embodiments, an external region comprises 3 nucleosides. In certain embodiments, an external region comprises 4 nucleosides. In certain embodiments, an external region comprises 5 nucleosides. In certain embodiments, an external region comprises 6 nucleosides. In certain embodiments, the internal region consists of 17 to 28 linked nucleosides. In certain embodiments, an internal region consists of 17 to 21 linked nucleosides. In certain embodiments, an internal region consists of 17 linked nucleosides. In certain embodiments, an internal region consists of 18 linked nucleosides. In certain embodiments, an internal region consists of 19 linked nucleosides. In certain embodiments, an internal region consists of 20 linked nucleosides. In certain embodiments, an internal region consists of 21 linked nucleosides. In certain embodiments, an internal region consists of 22 linked nucleosides. In certain embodiments, an internal region consists of 23 linked nucleosides. In certain embodiments, an internal region consists of 24 linked nucleosides. In certain embodiments, an internal region consists of 25 linked nucleosides. In certain embodiments, an internal region consists of 26 linked nucleosides. In certain embodiments, an internal region consists of 27 linked nucleosides. In certain embodiments, an internal region consists of 28 linked nucleosides.

miRNA Expression Vectors

Expression vectors that contain a miRNA sequence, or a precursor thereof, are also useful in the methods described herein, for the delivery of an miRNA or precursor thereof to a cell or tissue. Thus provided herein are expression vectors that comprise a miRNA sequence or a precursor thereof, optionally associated with a regulatory element that directs the expression of the miRNA sequence or precursor thereof. The choice of vector and/or expression control sequences to which the miRNA sequence, or precursor thereof, is operably linked depends on the functional properties desired, and the cell type to which the vector is to be delivered. In certain embodiments, the expression vector is a retroviral vector. In certain embodiments, the expression vector is an adenoviral vector. In certain embodiments, the expression vector is an adeno-associated viral vector. In certain embodiments, an expression vector encodes miR-34. In certain embodiments, an expression vector encodes a miR-34 precursor.

Certain Additional Therapies

Cancer treatments often comprise more than one therapy. As such, in certain embodiments the present invention provides methods for treating cancer comprising administering to a subject having cancer a composition comprising an oligomeric compound comprising an oligonucleotide having identity to a miRNA, or a precursor thereof, and further comprising administering at least one additional therapy.

In certain embodiments, an additional therapy is an anti-cancer therapy.

In certain embodiments, an anti-cancer therapy is chemotherapy. Suitable chemotherapeutic agents include docetaxel, cyclophosphamide, ifosfamide, methotrexate, vinblastine, cisplatin, 5-fluorouracil, gemcitabine, doxorubicine, mitomycin c, sorafenib, etoposide, carboplatin, epirubicin, irinotecan and oxaliplatin. An additional suitable chemotherapeutic agent includes an oligomeric compound, other than a composition of the present invention, that is used to treat cancer.

In certain embodiments, an anti-cancer therapy is radiation therapy. In certain embodiments, an anti-cancer therapy is surgical resection of a tumor.

In certain embodiments, an additional therapy may be designed to treat a disease other than cancer. In certain such embodiments, an additional therapy may be a treatment for hepatitis C infection or hepatitis B infection.

In certain embodiments, an additional therapy is a treatment for hepatitis C infection. Therapeutic agents for treatment of hepatitis C infection include interferons, for example, interferon alfa-2b, interferon alfa-2a, and interferon alfacon-1. Less frequent interferon dosing can be achieved using pegylated interferon (interferon attached to a polyethylene glycol moiety which significantly improves its pharmacokinetic profile). Combination therapy with interferon alfa-2b (pegylated and unpegylated) and ribavarin has also been shown to be efficacious for some patient populations. Other agents currently being developed include RNA replication inhibitors (e.g., ViroPharma's VP50406 series), antisense agents (for example, anti-miR-122), therapeutic vaccines, protease inhibitors, helicase inhibitors and antibody therapy (monoclonal and polyclonal).

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain such embodiments, the additional therapy is selected to treat or ameliorate a side effect of one or more compositions of the present invention. Such side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

In certain embodiments, one or more compositions of the present invention and one or more other pharmaceutical agents are administered at the same time. In certain embodiments, one or more compositions of the present invention and one or more other pharmaceutical agents are administered at different times. In certain embodiments, one or more compositions of the present invention and one or more other pharmaceutical agents are prepared together in a single formulation. In certain embodiments, one or more compositions of the present invention and one or more other pharmaceutical agents are prepared separately.

Certain Pharmaceutical Compositions

In certain embodiments, an oligomeric compound comprising an oligonucleotide having identity to a miRNA, or precursor thereof, described herein is prepared as a pharmaceutical composition for the treatment of cancer. Suitable administration routes include, but are not limited to, oral, rectal, transmucosal, intestinal, enteral, topical, suppository, through inhalation, intrathecal, intraventricular, intraperitoneal, intranasal, intraocular, intratumoral, and parenteral (e.g., intravenous, intramuscular, intramedullary, and subcutaneous). An additional suitable administration route includes chemoembolization. In certain embodiments, pharmaceutical intrathecals are administered to achieve local rather than systemic exposures. For example, pharmaceutical compositions may be injected directly in the area of desired effect (e.g., into a tumor).

In certain embodiments, a pharmaceutical composition of the present invention is administered in the form of a dosage unit (e.g., tablet, capsule, bolus, etc.). In certain embodiments, such pharmaceutical compositions comprise an oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of an oligonucleotide which has been prepared in water for injection, or in saline for injection, adjusted to pH 7.0-9.0 with acid or base during preparation, and then lyophilized. The lyophilized modified oligonucleotide may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising an oligonucleotide with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises an oligomeric compound in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more oligomeric compounds of the present invention is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Kits

The present invention also provides kits. In some embodiments, the kits comprise one or more compounds comprising an oligonucleotide consisting of 7 to 30 linked nucleosides, wherein the nucleobase sequence of the oligonucleotide has identity to miR-34. The compounds can be any of the compounds described herein, and can have any of the modifications described herein. In some embodiments, the compounds can be present within a vial. A plurality of vials, such as 10, can be present in, for example, dispensing packs. In some embodiments, the vial is manufactured so as to be accessible with a syringe. The kit can also contain instructions for using the compounds having identity to miR-34. In certain embodiments, the miR-34 is miR-34a, miR-34b or miR-34c.

In some embodiments, the kits may be used for administration of the compound to a subject. In such instances, in addition to compounds having identity to miR-34, the kit can further comprise one or more of the following: syringe, alcohol swab, cotton ball, and/or gauze pad. In some embodiments, the compounds having identity to miR-34 can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds having identity to miR-34. In certain embodiments, the miR-34 is miR-34a, miR-34b or miR-34c.

Certain Experimental Models

In certain embodiments, the present invention provides methods of using and/or testing modified oligonucleotides of the present invention in an experimental model. In certain embodiments, experimental models are employed to evaluate the effectiveness of modified oligonucleotides of the invention for the treatment of cancer. Those having skill in the art are able to select and modify the protocols for such experimental models to evaluate a pharmaceutical agent of the invention.

Generally, oligomeric compounds are first tested in cultured cells. Suitable cell types include those that are related to the cell type to which delivery of an oligonucleotide is desired in vivo. For example, suitable cell types for the study of oligomeric compounds for the treatment of cancer include cell types derived from liver cancer, such as HepG2, Hep3B, SK-Hep1, 7721, SNU-398, SNU423, SNU449, Huh7, HCCLM3 and MHT cells.

In certain embodiments, the extent to which an oligomeric compound mimics the activity of a miRNA is assessed in cultured cells. In certain embodiments, miRNA activity may be assessed by measuring the levels of the miRNA. Alternatively, the level of a predicted or validated miRNA target may be measured. miRNA activity may result in the down-regulation in the mRNA and/or protein of a miRNA target. Further, in certain embodiments, certain phenotypic outcomes may be measured. For example, suitable phenotypic outcomes include inhibition of cell proliferation, the induction of cell death, and/or the induction of apoptosis. Other suitable phenotypic outcomes include the arrest of cells at any point of the cell cycle, such as the G1/S transition, S phase, the G2/M transition, mitotic division, or cytokinesis. Following the in vitro identification of an oligomeric compound that effectively mimes the activity of a miRNA, oligomeric compounds are further tested in in vivo experimental models. Suitable experimental models for the testing of chemotherapeutic agents, including modified oligonucleotides complementary to a miRNA described herein, include: a subcutaneous xenograft mouse model, an orthotopic liver xenograft mouse model, an SV40 t/T transgenic mouse model, a TGF-α/c-myc transgenic mouse model and a chemically induced carcinogenic (diethylnitrosamine) mouse model.

A suitable in vivo experimental model for the testing of compositions of the present invention includes the subcutaneous xenograft mouse model. In this model, cells are removed from culture and injected subcutaneously into mice, where the cells form tumors. Suitable cells include, for example, liver cancer cells, such as Hep3B cells; lung cancer cells, such as H460 cells; and breast cancer cells. Suitable mice include, for example, BALB/c nude mice. A suitable injection site is, for example, the flank of the mouse. Oligomeric compound is administered to the mice at a frequency of 2 to 3 times per week. Oligomeric compound is administered prior to implantation, simultaneously with implantation, or after implantation. Suitable administration route include intraperitoneal administration and intratumoral administration. Oligomeric compound doses range from 0.5 to 50 mg/kg. The animals are treated for 3 to 4 weeks, after which tumor size, tumor number, and liver weight are measured. Measurements may be made with digital calipers. Saline-treated animals are used as a control group. A chemotherapeutic agent, such as, for example, 5-fluorouracil, may be used as a positive control for the inhibition of tumor size or number. Various endpoints are assessed, including tumor size, tumor number, and liver weight. Oligomeric compound-treated mice are compared to the same endpoints in control-treated mice. Statistical analyses are employed to identify significant differences in any of the endpoints. The subcutaneous xenograft model is an art-accepted model for the in vivo evaluation of chemotherapeutic agents, including oligonucleotides. See, for example, Koller et al., *Cancer Res.*, 2006, 66, 2059-2066, and Cheng et al., *Cancer Res.*, 2007, 67, 309-317. Orthotopic xenograft models may also be established using other liver-cancer derived cell lines, such as Hep3B or HepG2 cells. Such models may also be established using additional strains of mice, such as severe combined immunodeficiency (SCID) mice.

An additional in vivo experimental model for the testing of compositions of the invention is the CT26 liver metastasis model. In this model, an injection CT26 colon cancer cells into the spleen of BALB/c mice is quickly followed by a splenectomy. The cells pass through the splenic vein and into the portal vein and are deposited in the liver before they hit the general circulation. These cells can then form multiple metastases in the liver. See, for example, Xiang et al., *Cancer Res.*, 1997, 57, 4948-4955.

A suitable in vivo experimental model for the testing of compositions of the present invention is the HCCLM3 orthotopic liver xenograft model. In this model, approximately 1 million HCCLM3 cells (a highly metastatic human HCC cell line) are subcutaneously injected into the flanks of BALB/c nude mice. Once tumors are an appropriate size (e.g. 1 $mm^3$), tumor fragments are removed and intrahepatically implanted into other BALB/c nude mice. At this point, oligomeric compound is administered to the mice at a frequency of 2 to 3 times per week. Alternatively, administration of oligomeric compound begins several days (e.g. 10 days) following implantation. Suitable administration route include intraperitoneal administration and intratumoral administration. Oligomeric compound doses range from 5 to 50 mg/kg. The animals are treated for 3 to 4 weeks for a short term study, after which tumor size, tumor number, and liver weight are measured. Alternatively, the animals are treated for 8 to 30 weeks for a long term study, after which various endpoints are assessed, including tumor size, tumor number, liver weight, number of metastases and survival will be measured. Metastasis is measured in tissues such as lung tissue. Measurements of tumor size and weight may be made with digital calipers. Saline-treated animals are used as a control group. A chemotherapeutic agent, such as, for example, 5-fluorouracil, may be used as a positive control for the inhibition of tumor size or number. Endpoints observed in oligomeric compound-treated mice are compared to the same endpoints in control-treated mice. Statistical analyses are employed to identify significant differences in any of the endpoints. The orthotopic xenograft model is an art-accepted model for the in vivo evaluation of chemotherapeutic agents, including oligomeric compound. See, for example, Li et al., *Clin. Cancer Res.*, 2006, 12, 7140-7148. As an alternative to HCCLM3 cells, HepG2 cells may be used to establish the orthotopic model.

An additional suitable in vivo experimental model is the SV40 t/T transgenic mouse model. Transgenic mice have been engineered to express the SV40 large T antigen (SV40 t/T mice) under the control of the liver-specific C-reactive protein promoter (Ruther et al., *Oncogene*, 1993, 8, 87-93). The expression of SV40 large T antigen can be transiently induced by injection of bacterial lipopolysaccacharide, and results in the development of hepatocellular carcinoma. At this point, modified oligomeric compound is administered to the mice at a frequency of 2 to 3 times per week. Oligomeric compound doses range from 5 to 50 mg/kg. Suitable administration route include intraperitoneal administration and intratumoral administration. The animals are treated for 3 to 4 weeks for a short term study, after which tumor size, tumor number, and liver weight are measured. Alternatively, the animals are treated for 8 to 30 weeks for a long term study, after which various endpoints are measured, including tumor size, tumor number, liver weight, number of metastases, and survival. Metastasis is measured in tissues such as lung tissue. Measurements of tumor size and weight may be made with digital calipers. Saline-treated animals are used as a control group. A chemotherapeutic agent, such as, for example, 5-fluorouracil, may be used as a positive control for the inhibition of tumor size or number. Endpoints observed in oligomeric compound-treated mice are compared to the same endpoints in control-treated mice. Statistical analyses are employed to identify significant differences in any of the endpoints.

A suitable in vivo experimental model is a chemically-induced carcinogenic mouse model. In this model, liver cancer is induced by administration of the carcinogen diethylnitrosamine (DEN). Mice are injected intraperitoneally with 5 or 25 mg/kg DEN. Oligomeric compound, dissolved in saline, is administered to the mice at a frequency of 2 to 3 times per week. Oligomeric compound doses range from 5 to 50 mg/kg. Suitable administration route include intraperitoneal administration and intratumoral administration. The animals are treated for 4 to 8 weeks for a short term study, after which tumor size, tumor number, and liver weight are measured. Alternatively, the animals are treated for 8 to 30 weeks for a long term study, after which tumor size, tumor number, liver weight, number of metastases and survival will be measured. Metastasis is measured in tissues such as lung tissue. Measurements of tumor size and weight may be made with digital calipers. Saline-treated animals are used as a control group. A chemotherapeutic agent, such as, for example, 5-fluorouracil, may be used as a positive control for the inhibition of tumor size or number. Endpoints observed in oligomeric compound-treated mice are compared to the same endpoints in control-treated mice. Statistical analyses are employed to identify significant differences in any of the endpoints. The DEN-induced HCC model has been used for the study of HCC. See, for example, Maeda et al., *Cell*, 2005, 121, 977-990.

Certain Quantitation Assays

The effects of administration of a miRNA mimic may be assessed by a variety of methods known in the art. In certain embodiments, these methods are be used to quantitate miRNA levels in cells or tissues in vitro or in vivo. In certain embodiments, changes in miRNA levels are measured by microarray analysis. In certain embodiments, changes in miRNA levels are measured by one of several commercially available PCR assays, such as the TaqMan® MicroRNA Assay (Applied Biosystems). In certain embodiments, miRNA activity is assessed by measuring the mRNA and/or protein level of a target of a miRNA. Addition of a miRNA mimic generally results in the down-regulation of the level of mRNA and/or protein of a target of the miRNA.

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The following examples are presented in order to more fully illustrate some embodiments of the invention. They should, in no way be construed, however, as limiting the broad scope of the invention.

EXAMPLES

Example 1 miR-34 Mimic Compositions

Compositions comprising miR-34 mimics were designed for use in the methods described herein. Such compositions are illustrated in Table 1. The oligomeric compounds shown in Table 1 are comprised of an oligonucleotide hybridized to a complementary oligonucleotide, where the 3' terminus of each of the oligonucleotide and complementary oligonucleotide has a two nucleoside overhang. The oligonucleotide and complementary oligonucleotide consist of unmodified RNA nucleosides linked through phosphodiester linkages. Lipid to compound ratio is expressed as the ratio of lipid weight to oligomeric compound weight. For example, a lipid:compound ratio of 11:1 means 11 times as much lipid as oligomeric compound by weight.

Example 2

Evaluation of miR-34 Mimic Activity in Cultured Cells

Cell Cycle Block in A549 Cells

To evaluate the effects of introducing a miR-34a mimic into cells, A549 cells were transfected with double-strand miR-34a mimics. After treatment with a miR-34a mimic, cells were treated with nocodazole, to synchronize the cells at the G2/M transition of the cell cycle. The miR-34a mimic used in this study was a double-stranded oligomeric compound, comprised of the miR-34a sequence hybridized to a complementary oligonucleotide.

Cultured A549 cells received one of several treatments: 1) PBS; 2) nocodazole at a concentration of 0.1 to 2.0 ng/ml; or 3) nocodazole at a concentration of 0.1 to 2.0 ng/ml and 5 nM miR-34a mimic. Approximately 24 hours after treatment, cells were harvested, and DNA content was measured to determine how many cells in each population were at each stage of the cell cycle. RNA was isolated, and used for microarray profiling.

Treatment with miR-34-1 blocked cells in the G1 phase of the cell cycle. Microarray profiling revealed that miR-34a-1 down-regulated transcripts containing the seed match 'ACT-GCC,' demonstrating that miR-34a-1 was regulating expected targets of miR-34a. These results demonstrate that miR-34a-1 regulates expected miR-34a target transcripts, and also plays a role in cell cycle regulation.

Cell Cycle Block Analysis in HepG2 cells and Hep3B Cells

To evaluate the effects of introducing a miR-34a mimic into cells with and without functional p53, a cell cycle block experiment was performed using either HepG2 cells, which are p53-expressing cells, or Hep3B cells, which are p53-

TABLE 1

Compositions comprising miR-34 mimics

| Identifier | Oligomeric compound | SEQ ID NO: | Lipid | Lipid: Compound Ratio |
|---|---|---|---|---|
| miR-34a-1 | UGGCAGUGUCUUAGCUGG-UUGU | 1 | None | |
| | AAACCGUCACAGAAUCGACCAA | 7 | | |
| miR-34a-L06 | UGGCAGUGUCUUAGCUGG-UUGU | 1 | XTC/DSPC/Chol/PEG-DMG | 11 |
| | AAACCGUCACAGAAUCGACCAA | 7 | 57.5/7.5/31.5/3.5 | |
| miR-34a-L07 | UGGCAGUGUCUUAGCUGG-UUGU | 1 | XTC/DSPC/Chol/PEG-DMG | 6 |
| | AAACCGUCACAGAAUCGACCAA | 7 | 60/7.5/31/1.5 | |
| miR-34a-L08 | UGGCAGUGUCUUAGCUGG-UUGU | 1 | XTC/DSPC/Chol/PEG-DMG | 11 |
| | AAACCGUCACAGAAUCGACCAA | 7 | 60/7.5/31/1.5 | |
| miR-34a-L09 | UGGCAGUGUCUUAGCUGG-UUGU | 1 | XTC/DSPC/Chol/PEG-DMG | 11 |
| | AAACCGUCACAGAAUCGACCAA | 7 | 50/10/38.5/1.5 | |
| miR-34a-mm1 | TGCGAGTGTCTTAGCTGGT-TGT | 8 | None | |
| | AAACGCTCACAGAATCGACCAA | 9 | | |
| miR-34a-mm1L09 | TGCGAGTGTCTTAGCTGGT-TGT | 8 | XTC/DSPC/Chol/PEG-DMG | 11 |
| | AAACGCTCACAGAATCGACCAA | 9 | 50/10/38.5/1.5 | |

"mm" indicates a sequence containing mismatches relative to the miR-34 sequence deficient cells. Cells were transfected with miR-34a-1 mimic at a concentration of 25 nM, 5 nM, 1 nM, 0.2 nM, 0.04 nM, or 0.008 nM, in the presence of a lipid transfection reagent. After 24 hours of treatment with the miR-34a mimic, cells were treated with nocodazole, to synchronize the cells at the G2/M transition of the cell cycle. After approximately 16 hours of nocodazole treatment, cells were harvested, fixed, stained with propidium iodide. Cell cycle phase was determined using a flow cytometer.

Treatment with miR-34-1 blocked cells in the G1 phase of the cell cycle, in both p53-expressing HepG2 and p53-deficient Hep3B cells, indicating that replacement of miR-34a in the presence or absence of functional p53 leads to a cell cycle arrest. The cell cycle arrest was stronger in the p53-expressing cells, suggesting that although miR-34a mimic treatment can induce a cell cycle arrest in the presence or absence of p53, the effects of miR-34a mimic treatment may be more robust in a p53-expressing cancer.

Example 3

Delivery of miR-34 Mimic to Liver

Compositions of the invention were tested for delivery to and activity in the liver. The lipid-containing composition miR-34a-L09 was tested in this study.

Wild-type mice were administered one of several treatments: 1) saline; 2) miR-34a-L09 at a dose of 1 mg/kg oligomeric compound; 3) miR-34a-L09 at a dose of 2 mg/kg oligomeric compound; or 4) miR-34a-L09 at a dose of 3 mg/kg oligomeric compound. Each treatment group included 3-4 mice per group. Treatments were administered intravenously, twice per week for four weeks (a total of 8 doses). Mice were sacrificed 24 hours following the final dose. Serum, liver tissue, and spleen tissue were collected. RNA was isolated from liver tissue.

Toxicity parameters were evaluated. No changes in total body weight were observed, and only mild increases in ALT and ALT were observed (no increases above 3 times the upper limit of normal). Increases in inflammatory markers (eg Ifit2 and Usp18) were observed, but were not of a high magnitude and were not dose-proportional.

miR-34a copy number was measured by real-time PCR. The miR-34a-L09 treatments delivered copies of miR-34a in a dose-dependent manner. The 3 mg/kg dose delivered approximately 50,000 copies of miR-34a per cell equivalent.

Microarray profiling of liver RNA samples revealed that the mean expression of the top 100 miR-34 seed-matched transcripts was strongly shifted downward.

These results demonstrate that treatment with multiple doses of lipid-based compositions of miR-34a mimic led to an accumulation of miR-34a in the liver, and a miR-34-specific down-regulation of target transcripts.

Example 4

Orthotopic Xenograft Model

Compositions of the invention were tested in an orthotopic liver tumor model in which human hepatoma cells (Hep3B) were implanted into livers of immunocompromised mice (SCID mice).

Alpha-Fetoprotein as a Marker for Tumor Size

Hep3B cells that are implanted into the livers of immunocompromised mice secrete human alpha-fetoprotein (aFP). To determine whether human aFP circulating in the serum of the mice could be used to assess tumor size, orthotopic tumors were established, and aFP was measured after 20, 30, or 40 days after implantation. Tumor weight was measured at the end of the study (40 days post-implantation) and compared to circulating human aFP.

It was found that circulating human aFP levels increased with time (FIG. 1). Additionally, aFP levels correlated to tumor size (see Table 2 below). Thus, aFP may be used as a determinant of tumor size, and further may be used to sort animals into groups of similar aFP levels.

TABLE 2

Tumor weight correlates with aFP levels

| animal # | aFP (ng/mL) | tumor size (mg) |
|---|---|---|
| 1 | 117415 | 470 |
| 2 | 90746 | 243 |
| 4 | 65644 | 188 |
| 5 | 26343 | 41 |
| 3 | 10897 | 29 |

Orthotopic Study #1

Approximately $1 \times 10^6$ Hep3B cells were surgically implanted directly into the livers of SCID mice. Three weeks following tumor cell implantation, mice were administered saline or miR-34a-L09 at a dose to provide 1 mg/kg oligomeric compound, once per day for three consecutive days. Mice were sacrificed 24 hours following the third and final dose of miR-34a-LNP09. Liver and tumor tissues were collected. RNA was isolated, and subjected to microarray profiling. Analysis of the microarray profiles revealed that as a population, the most highly down-regulated miR-34 seed match transcripts from the in vitro study of Example 2 were also significantly down-regulated as a population in the orthotopic tumors.

Figure 2:
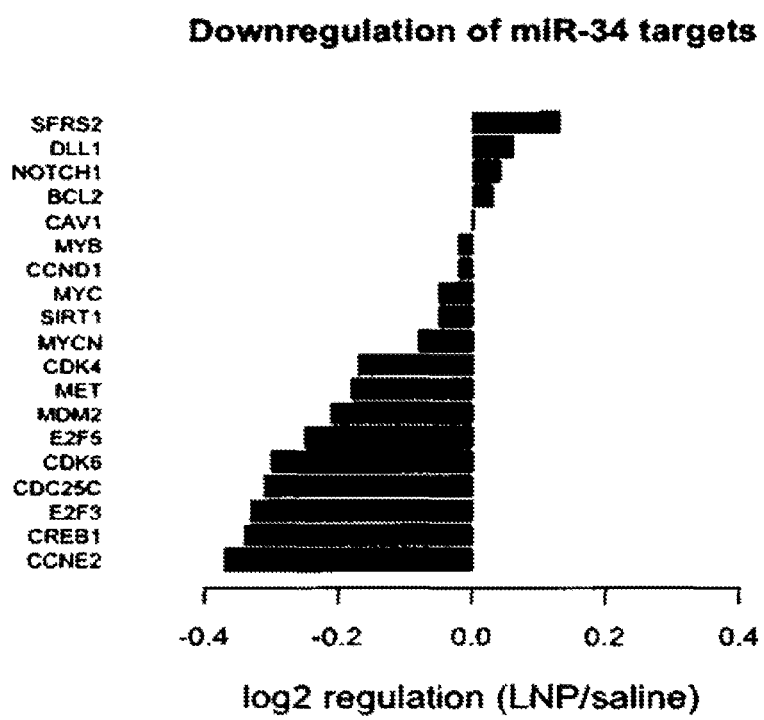
FIG. 2: Treatment with miR-34a-L09 led to down-regulation of multiple miR-34 targets in liver tumors. The mean log ratios of target regulation in tumors from three miR-34a-LNP09-treated mice, relative to three saline-treated animals. Significance was determined by T-test.
Figure 3:
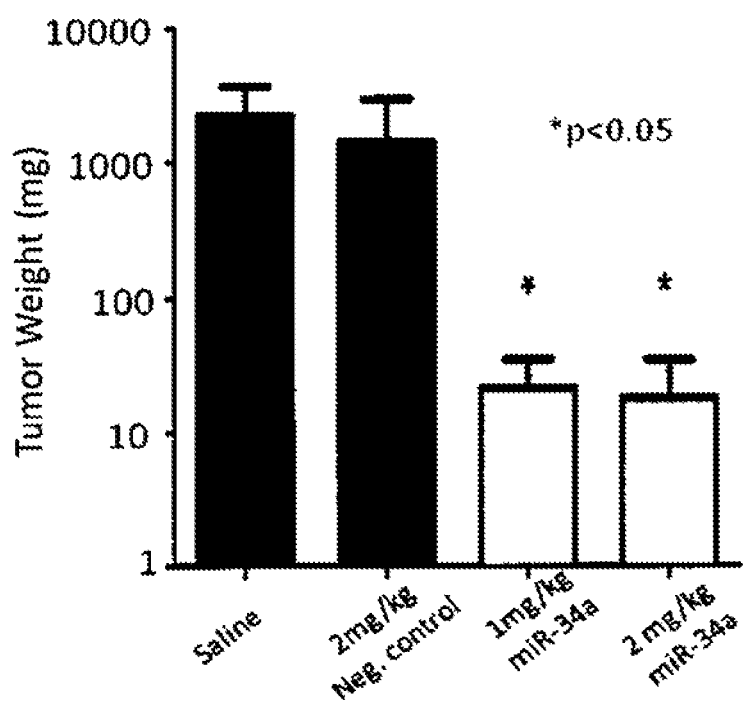
FIG. 3: miR-34 replacement inhibits liver tumor growth. Treatment with either 1 mg/kg or 2 mg/kg of lipid formulated miR-34a (miR-34a-L09) significantly inhibited tumor growth, as judged by comparison of tumor weight and size relative to control-treated samples.

Treatment with miR-34a-L09 led to down-regulation of multiple miR-34 seed match transcripts in liver tumors. Shown in FIG. 2 are the mean log ratios of seed match transcript regulation in tumors from three miR-34a-LNP09-treated mice, relative to three saline-treated animals. The upregulated and down regulated genes are also shown in Tables 3 and 4, respectively. Significance was determined by T-test. Cell cycle and mitotic genes were over-represented in one cluster of down-regulated genes (see Table 4 below).

TABLE 3

Up-Regulated Targets

| Gene Symbol | Gene Name | range of mean log ratio of target regulation |
|---|---|---|
| SFRS2 | Splicing factor, arginine/serine-rich 2 | 0.0 to 0.2 |
| DLL1 | delta-like 1 | 0.0 to 0.1 |
| NOTCH1 | Notch homolog 1, translocation-associated | 0.0 to 0.1 |
| BCL2 | B-cell lymphoma 2 | 0.0 to 0.1 |
| CAV1 | caveolin 1 | 0.0 to 0.1 |

TABLE 4

Down-Regulated Targets

| Gene Symbol | Gene Name | range of mean log ratio of target regulation |
|---|---|---|
| MYB | v-myb myeloblastosis viral oncogene homolog | 0.0 to −0.1 |
| CCND1 | cyclin D1 | 0.0 to −0.1 |
| MYC | myelocytomatosis viral oncogene | 0.0 to −0.1 |
| SIRT1 | sirtuin | 0.0 to −0.1 |
| MYCN | V-myc myelocytomatosis viral related oncogene, neuroblastoma derived | 0.0 to −0.1 |
| CDK4 | cyclin-dependent kinase 4 | −0.1 to −0.2 |
| MET | met proto-oncogene | −0.1 to −0.2 |
| MDM2 | mouse double minute, human homolog | −0.2 to −0.3 |
| E2F5 | E2F transcription factor 5 | −0.2 to −0.3 |
| CDK6 | cyclin-dependent kinase 6 | −0.2 to −0.3 |
| CDC25C | cell division cycle 25 homolog | −0.3 to −0.4 |
| E2F3 | E2F transcription factor 3 | −0.3 to −0.4 |
| CREB1 | cAMP responsive element binding protein 1 | −0.3 to −0.4 |
| CCNE2 | cyclin E2 | −0.3 to −0.4 |

These results demonstrate that the administration of miR-34a-L09 resulted in delivery of miR-34 mimic to cells of the liver tumor, and was active in down-regulating miR-34 seed-matched transcripts. Thus the compositions described herein are useful for the delivery of compositions comprising miRNA mimics to tumor cells, and for the treatment of cancer.

Orthotopic Study #2

Experimental Design

Approximately $1 \times 10^6$ Hep3B cells were surgically implanted directed into the livers of SCID mice. Ten days following implantation of the Hep3B cells, plasma was collected to measure levels of circulating human alpha-fetoprotein (aFP; measured by ELISA). Mice with similar aFP levels were placed into groups of 4 animals each. Each group received one of four treatments: (1) saline; (2) negative control oligonucleotide (miR-34a mm1 L09) at a dose of 2 mg/kg of oligomeric compound; (3) miR-34a-L09 at a dose of 1 mg/kg of oligomeric compound; or (4) miR-34a-L09 at a dose of 2 mg/kg of oligomeric compound. Treatments were administered intravenously twice per week. Just prior to dosing and at weeks 1, 2, 3, and 4 of the study, aFP, ALT, AST, bilirubin, BUN, and cholesterol levels were measured in each animal. Animals were sacrificed 24 hours following the $8^{th}$ and final dose. Body, liver, spleen, weights were recorded. Tumor size and weights were recorded. Plasma was also collected at the end of the study, for measurement of AST, ALT, bilirubin, cholesterol, BUN, and aFP levels. RNA was isolated from liver tissue and tumor tissue, for analysis of miR-34a levels, miR-34 target gene expression, and inflammatory markers. miR-34a levels were measured by RT-PCR.

Results

Treatment with either 1 mg/kg or 2 mg/kg miR-34a-L09 significantly inhibited tumor growth, as judged by comparison of tumor weight and size relative to control-treated samples. As shown in FIG. 1 and Table 5, replacement of miR-34a in liver tumors led to a statistically significant inhibition of tumor growth.

TABLE 5 tumor weight (mg)

| Animal # | Saline | miR34a mismatch control 2 mg/kg | miR34a 1 mg/kg | miR34a 2 mg/kg |
|---|---|---|---|---|
| 1 | 538 | 60 | 61 | 1 |
| 2 | 2902 | 3561 | 19 | 69 |
| 3 | 3202 | 619 | 7 | 0 |
| 4 | * | 1475 | 0 | 3 |
| average | 2214 | 1413 | 29 ($p < 0.05$) | 23 ($p < 0.05$) |

* Animal died prior to study completion

Additionally, treatment with miR-34aL09 significantly reduced circulating human aFP levels.

TABLE 6 miR-34a treatment reduced circulating aFP levels circulating human aFP (mg/dL)

| Treatment Group | Week | Animal #1 | Animal #2 | Animal #3 | Animal #4 | Average |
|---|---|---|---|---|---|---|
| Saline | 0 | 387 | 2257 | 1088 | 1419 | 1288 |
|  | 1 | 5904 | 10977 | 13457 | 11872 | 10553 |
|  | 2 | 16879 | 61202 | 51588 | 53476 | 45786 |
|  | 3 | 139598 | 971208 | 682405 | 730668 | 630970 |
|  | 4 | 436792 | 1012525 | 1090661 | * | 846659 |
| miR-34a mismatch 2 mg/kg | 0 | 552 | 2054 | 779 | 2193 | 1395 |
|  | 1 | 8599 | 4205 | 5387 | 24699 | 10723 |
|  | 2 | 32313 | 6852 | 8828 | 71231 | 29806 |
|  | 3 | 478442 | 214982 | 139795 | 971208 | 451107 |
|  | 4 | 310927 | 1039183 | 301441 | 1248611 | 725041 |
| miR-34a 1 mg/kg | 0 | 515 | 2056 | 848 | 1840 | 1315 |
|  | 1 | 12071 | 6937 | 7297 | 4967 | 7818 |
|  | 2 | 24460 | 11749 | 10351 | 8401 | 13740 |
|  | 3 | 151232 | 97952 | 36247 | 96932 | 95591 |
|  | 4 | 364382 | 320158 | 32733 | 35653 | 188231 |
| miR-34a 2 mg/kg | 0 | 809 | 2147 | 838 | 1110 | 1226 |
|  | 1 | 5428 | 5059 | 10507 | 6870 | 6966 |
|  | 2 | 7524 | 8199 | 17471 | 12024 | 11305 |
|  | 3 | 68586 | 59934 | 91899 | 24229 | 61162 |
|  | 4 | 90551 | 216606 | 37265 | 34942 | 94841 |

* Animal died prior to study completion

Treatment with miR-34 also maintained normal liver function, compared to the saline-treated group which exhibited increased total bilirubin and ALT, which are indicative of liver function abnormalities. For example, as shown in Table 7, bilirubin increased throughout the study period in the saline-treated and miR-34a mm-treated animals, but did not increase in the miR-34a-treated animals.

TABLE 7

Bilirubin levels did not increase in miR-34a treated animals

Total Bilirubin (mg/dL)

| Treatment Group | Week | Animal #1 | Animal #2 | Animal #3 | Animal #4 | Average |
|---|---|---|---|---|---|---|
| Saline | 0 | 0.14 | 0.19 | 0.21 | 0.14 | 0.17 |
|  | 1 | 0.19 | 0.21 | 0.24 | 0.21 | 0.21 |
|  | 2 | 0.14 | 0.19 | 0.26 | 0.29 | 0.22 |
|  | 3 | 0.43 | 0.28 | 0.24 | 0.31 | 0.32 |
|  | 4 | 0.23 | 0.6 | 0.53 | * | 0.45 |
| miR-34a mismatch 2 mg/kg | 0 | 0.11 | 0.14 | 0.19 | 0.19 | 0.16 |
|  | 1 | 0.16 | 0.16 | 0.21 | 0.21 | 0.19 |
|  | 2 | 0.09 | 0.21 | 0.19 | 0.26 | 0.19 |
|  | 3 | 0.24 | 0.26 | 0.36 | 0.21 | 0.27 |
|  | 4 | 0.26 | 0.46 | 0.36 | 0.38 | 0.37 |

TABLE 7-continued

Bilirubin levels did not increase in miR-34a treated animals

| Treatment Group | Week | Animal #1 | Animal #2 | Animal #3 | Animal #4 | Average |
|---|---|---|---|---|---|---|
| | | | Total Bilirubin (mg/dL) | | | |
| miR-34a 1 mg/kg | 0 | 0.21 | 0.11 | 0.16 | 0.16 | 0.16 |
| | 1 | 0.21 | 0.21 | 0.14 | 0.18 | 0.19 |
| | 2 | 0.14 | 0.18 | 0.16 | 0.16 | 0.16 |
| | 3 | 0.11 | 0.14 | 0.14 | 0.16 | 0.14 |
| | 4 | 0.11 | 0.09 | 0.21 | 0.14 | 0.14 |
| miR-34a 2 mg/kg | 0 | 0.21 | 0.19 | 0.21 | 0.16 | 0.19 |
| | 1 | 0.21 | 0.21 | 0.18 | 0.16 | 0.19 |
| | 2 | 0.14 | 0.31 | 0.14 | 0.19 | 0.20 |
| | 3 | 0.26 | 0.43 | 0.11 | 0.14 | 0.24 |
| | 4 | 0.18 | 0.19 | 0.21 | 0.11 | 0.17 |

* Animal died prior to study completion

TABLE 8

AST levels did not increase in miR-34a treated animals

| Treatment Group | Week | Animal #1 | Animal #2 | Animal #3 | Animal #4 | Average |
|---|---|---|---|---|---|---|
| | | | AST (U/L) | | | |
| Saline | 0 | 28 | 20 | 23 | 29 | 25 |
| | 1 | 28 | 30 | 21 | 98 | 44 |
| | 2 | 18 | 37 | 33 | 28 | 29 |
| | 3 | 128 | 69 | 31 | 20 | 62 |
| | 4 | 46 | 175 | 75 | * | 99 |
| miR-34a mismatch 2 mg/kg | 0 | 16 | 27 | 26 | 28 | 24 |
| | 1 | 35 | 23 | 23 | 21 | 26 |
| | 2 | 46 | 35 | 49 | 88 | 55 |
| | 3 | 39 | 51 | 26 | 43 | 40 |
| | 4 | 37 | 71 | 51 | 146 | 76 |
| miR-34a 1 mg/kg | 0 | 22 | 20 | 15 | 31 | 23 |
| | 1 | 29 | 39 | 29 | 15 | 21 |
| | 2 | 17 | 30 | 17 | 24 | 23 |
| | 3 | 36 | 22 | 18 | 21 | 22 |
| | 4 | 30 | 20 | 36 | 23 | 23 |
| miR-34a 2 mg/kg | 0 | 17 | 25 | 22 | 15 | 27 |
| | 1 | 20 | 40 | 21 | 34 | 31 |
| | 2 | 20 | 39 | 24 | 33 | 29 |
| | 3 | 40 | 22 | 23 | 20 | 28 |
| | 4 | 29 | 30 | 30 | 35 | 35 |

* Animal died prior to study completion miR-34 was effectively delivered to both the liver and tumor of animals treated with miR-34-LNP09. miR-34 was detected by PCR, and the PCR primers can hybridize to the miR-34a mismatch oligonucleotide as well as the miR-34 sequence, thus the miR-34a mismatch compound can be detected. However, due to the mismatches, the miR-34a mismatch compound does not mimic miR-34a activity.

TABLE 9 miR-34a copy number in liver

| Animal # | Saline | miR34a mismatch control 2 mg/kg | miR34a 1 mg/kg | miR34a 2 mg/kg |
|---|---|---|---|---|
| 1 | 142 | 55100 | 29100 | 42200 |
| 2 | 138 | 49300 | 45900 | 57300 |
| 3 | 143 | 55300 | 21500 | 70200 |
| 4 | | 49000 | 28900 | 55500 |
| average | 141 | 53233 | 32167 | 56567 |

TABLE 10 miR-34a copy number in tumor

| Animal # | Saline | miR34a mismatch control 2 mg/kg | miR34a 1 mg/kg | miR34a 2 mg/kg |
|---|---|---|---|---|
| 1 | 288 | 35900 | 14000 | 1190 |
| 2 | 186 | 47100 | 7780 | 31700 |
| 3 | 114 | 28500 | 2730 | 17800 |
| 4 | * | 23200 | ** | ** |
| average | 196 | 37167 | 8170 | 16897 |

* Animal died prior to study completion
** No visible tumors were present in the livers of these animals miR-34a-L09 treatment also reduced liver expression of a well-characterized miR-34 target transcript, cMet, relative to saline treatment and mismatch control treatment. cMet was measured by PCR, and cMet in each sample normalized to total RNA level in the sample.

TABLE 11

Normalized levels of liver cMet

| Animal # | Saline | miR34a mismatch control 2 mg/kg | miR34a 1 mg/kg | miR34a 2 mg/kg |
|---|---|---|---|---|
| 1 | 0.077 | 0.058 | 0.040 | 0.028 |
| 2 | 0.063 | 0.071 | 0.036 | 0.009 |
| 3 | 0.100 | 0.092 | 0.019 | 0.029 |
| 4 | * | 0.099 | 0.049 | 0.024 |
| Average | 0.080 | 0.074 | 0.031 | 0.022 |

* Animal died prior to study completion

The results of this study demonstrate that miR-34a can be effectively delivered to the liver, and to tumors within the liver. The introduction of miR-34a into the tumor cells resulted in the down-regulation of transcripts containing miR-34 heptamer seed matches, and these transcripts were over-represented among the down-regulated genes. Additionally, replacement of miR-34a in liver tumors inhibited tumor growth, normalized liver function and reduced circulating aFP levels.

Accordingly, provided herein are compositions comprising miR-34a mimics, and methods for their use in the treatment of cancer.

Example 5

Effects of miR-34a on Myc Expression

The Myc gene encodes a transcription factor. Aberrant expression of Myc leads to the unregulated expression of many genes which are involved in the control of cell growth. In many cancers, Myc is mutated and consequently inappropriately expressed, thus Myc is considered to be an oncogene which contributes to the formation of cancer.

As demonstrated in Example 4, Myc transcript was down-regulated following introduction of LNP-formulated miR-34a mimic into cultured Hep3B cells. To determine whether Myc protein was also reduced, proteins were isolated from the cells and subject to western blotting. Protein amounts in each experimental sample were normalized to the amount of vinculin protein detected in each sample. Detection of Myc protein revealed a strong reduction of Myc protein in the cells into which miR-34a mimic was introduced. Accordingly, introduction of a miR-34a mimic into cancer-derived cells results in the reduction of the known oncogene Myc.

What is claimed is:

1. A method of treating liver cancer comprising intravenously administering to a subject having liver cancer a composition comprising an oligomeric compound comprising a first oligonucleotide consisting of 19 to 23 linked nucleosides, wherein the nucleobase sequence of the first oligonucleotide has at least 90% identity with the nucleobase sequence of SEQ ID NO: 1 with 100% identity with nucleobases 2 to 7 of SEQ ID NO: 1, wherein the oligomeric compound comprises a second oligonucleotide hybridized to the first oligonucleotide, wherein the second oligonucleotide consists of 19 to 23 linked nucleosides and wherein the second oligonucleotide is complementary to the first oligonucleotide, and wherein the oligomeric compound is formulated in a liposome.

2. The method of claim 1 wherein the liver cancer is hepatocellular carcinoma.

3. The method of claim 1 wherein the subject is a human.

4. The method of claim 1 comprising administering at least one additional therapy.

5. The method of claim 4 wherein the at least one additional therapy comprises a chemotherapeutic agent.

6. The method of claim 5 wherein the chemotherapeutic agent is selected from 5-fluorouracil, gemcitabine, doxorubicine, mitomycin c, sorafenib, etoposide, carboplatin, epirubicin, irinotecan and oxaliplatin.

7. The method of claim 1 comprising selecting a subject having a p-53 deficient cancer.

8. The method of claim 1, wherein the liposome comprises at least one lipid selected from phosphatidylcholine (PC), 1,2-Dioleoyl-sn-glycero-3-phosphocholine (DOPC), lecithin, phosphatidylethanolamine (PE), lysolecithin, lysophosphatidylethanolamine, sphingomyelin (SM), cardiolipin, phosphosphatidic acid, 1,2-Distearoyl-sn-glycero-3-phosphocholine (DSPC), 1,2-Dipalmitoyl-sn-glycero-3-phosphoethanolamine (DPPE), 1-Palmitoyl-2-oleoyl-sn-glycero-3-phosphocholine (POPC), 1,2-Dilauroyl-sn-glycero-3-phosphocholine (DLPC), 1,2-Dimyristoyi-sn-glycero-3-phosphocholine (DMPC), 1,2-Dipalmitoyl-sn-glycero-3-phosphocholine (DPPC), 1,2-Dimyristoyl-sn-glycero-3-phosphoethanolamine (DMPE), 1,2-Dioleoyl-sn-glycero-3-phosphoethanolamine (DOPE), dipalmitoloeoyl-PE, diphytanoyl-PE, DSPE, dielaidoyl-PE, dilinoleoyl-SM, and dilinoleoyl-PE.

9. The method of claim 1, wherein the complementary oligonucleotide comprises a 5' terminus cap or a 3' terminus cap, or a 5' terminus cap and a 3' terminus cap.

10. The method of claim 9, wherein the complementary oligonucleotide comprises a 5' terminus cap.

11. The method of claim 9, wherein the cap is selected from a 4',5'-methylene nucleotide, a 1-(beta-D-erythrofuranosyl) nucleotide, a 4'-thio nucleotide, a carbocyclic nucleotide, a 1,5-anhydrohexitol nucleotide, an L-nucleotide, an alpha-nucleotide, a modified base nucleotide, a phosphorodithioate linkage, a threo-pentofuranosyl nucleotide, an acyclic 3',4'-seco nucleotide, an acyclic 3,4-dihydroxybutyl nucleotide, an acyclic 3,5-dihydroxypentyl nucleotide, a 3'-3'-inverted nucleotide moiety, a 3'-3'-inverted abasic moiety, a 3'-2'-inverted nucleotide moiety, a 3'-2'-inverted abasic moiety, a 1,4-butanediol phosphate, a 3'-phosphoramidate, a hexylphosphate, an aminohexyl phosphate, a 3'-phosphate, a 3'-phosphorothioate, a phosphorodithioate, a bridging methylphosphonate moiety, and a non-bridging methylphosphonate moiety 5'-amino-alkyl phosphate, a 1,3-diamino-2-propyl phosphate, 3-aminopropyl phosphate, a 6-aminohexyl phosphate, a 1,2-aminododecyl phosphate, a hydroxypropyl phosphate, a 5'-5'-inverted nucleotide moiety, a 5'-5'-inverted abasic moiety, a 5'-phosphoramidate, a 5'-phosphorothioate, a 5'-amino, a bridging and/or non-bridging 5'-phosphoramidate, a phosphorothioate, and a 5'-mercapto moiety.

12. The method of claim 1, wherein the complementary oligonucleotide is at least 90% complementary to the oligonucleotide.

13. The method of claim 1, wherein the complementary oligonucleotide is 100% complementary to the oligonucleotide.

14. The method of claim 1, wherein the central complementary region of the oligomeric compound has 0, 1, or 2 mismatches between the oligonucleotide and the complementary oligonucleotide.

15. The method of claim 1, wherein the hybridization of the complementary oligonucleotide to the oligonucleotide forms an overhang at each 3' terminus, wherein the overhang has two nucleosides.

* * * * *

UNITED STATES PATENT AND TRADEMARK OFFICE
CERTIFICATE OF CORRECTION

PATENT NO. : 8,846,631 B2  
APPLICATION NO. : 13/521597  
DATED : September 30, 2014  
INVENTOR(S) : Eric G. Marcusson et al.

Page 1 of 1

It is certified that error appears in the above-identified patent and that said Letters Patent is hereby corrected as shown below:

On the Title Page, the listing of the Assignee in item (73) should be deleted and replaced with:

(73) Assignee: Regulus Therapeutics Inc., San Diego, CA (US)  
Alnylam Pharmaceuticals, Cambridge, MA (US)

Signed and Sealed this  
Thirtieth Day of December, 2014

Michelle K. Lee  
*Deputy Director of the United States Patent and Trademark Office*